US009095269B2

(12) United States Patent
Morita

(10) Patent No.: US 9,095,269 B2
(45) Date of Patent: Aug. 4, 2015

(54) IMAGE PROCESSING DEVICE, IMAGE PROCESSING METHOD, AND PROGRAM

(75) Inventor: Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 429 days.

(21) Appl. No.: 13/069,817

(22) Filed: Mar. 23, 2011

(65) Prior Publication Data

US 2011/0235877 A1    Sep. 29, 2011

(30) Foreign Application Priority Data

Mar. 23, 2010 (JP) .................................. 2010-65925

(51) Int. Cl.
*G06K 9/00* (2006.01)
*A61B 1/05* (2006.01)
*A61B 1/00* (2006.01)
*G06T 5/00* (2006.01)
*G06T 5/50* (2006.01)

(52) U.S. Cl.
CPC ............... *A61B 1/05* (2013.01); *A61B 1/00009* (2013.01); *G06T 5/002* (2013.01); *G06T 5/50* (2013.01); *G06T 2207/10068* (2013.01); *G06T 2207/20182* (2013.01); *G06T 2207/20192* (2013.01); *G06T 2207/20221* (2013.01); *G06T 2207/30101* (2013.01)

(58) Field of Classification Search
CPC ...... A61B 1/00009; A61B 1/05; G06T 5/002; G06T 5/50; G06T 2207/10068; G06T 2207/20182; G06T 2207/20192; G06T 2207/20221; G06T 2207/30101
See application file for complete search history.

(56) References Cited

U.S. PATENT DOCUMENTS

| 7,289,140 | B2 * | 10/2007 | Kobayashi | ...................... | 348/68 |
| 7,385,767 | B2 * | 6/2008 | Minakata | ...................... | 359/678 |
| 7,469,160 | B2 * | 12/2008 | Banks et al. | .................. | 600/476 |
| 7,564,602 | B2 * | 7/2009 | Ota et al. | ...................... | 358/518 |

(Continued)

FOREIGN PATENT DOCUMENTS

| JP | 11-136693 A | 5/1999 | | |
| JP | 2000-148987 | * 5/2000 | ................ | G06T 1/00 |

(Continued)

OTHER PUBLICATIONS

Machine translation of JP2000-148987.*

(Continued)

*Primary Examiner* — Katrina Fujita
(74) *Attorney, Agent, or Firm* — Scully, Scott, Murphy & Presser, P.C.

(57) ABSTRACT

An image processing device includes a normal light image acquisition section that acquires a normal light image that includes an object image and includes information within a wavelength band of white light, a special light image acquisition section that acquires a special light image that includes an object image and includes information within a specific wavelength band, a correction section that performs a correction process on the special light image, and a blending section that performs a blending process that blends the normal light image and a corrected special light image that is the special light image corrected by the correction section. The blending section blends a component G of the normal light image and a component G of the corrected special light image, and blends a component B of the normal light image and a component B of the corrected special light image.

19 Claims, 18 Drawing Sheets

(56) References Cited

U.S. PATENT DOCUMENTS

| | | | |
|---|---|---|---|
| 8,279,275 B2* | 10/2012 | Gono et al. | 348/65 |
| 8,289,421 B2* | 10/2012 | On | 348/241 |
| 8,531,512 B2* | 9/2013 | Gono et al. | 348/68 |
| 2004/0225222 A1* | 11/2004 | Zeng et al. | 600/476 |
| 2005/0206978 A1* | 9/2005 | Sone | 358/516 |
| 2008/0306338 A1* | 12/2008 | Yamazaki et al. | 600/109 |
| 2009/0202124 A1* | 8/2009 | Matsuda et al. | 382/128 |
| 2010/0063355 A1* | 3/2010 | Matsuura | 600/109 |
| 2010/0079615 A1* | 4/2010 | Hatakeyama | 348/223.1 |

FOREIGN PATENT DOCUMENTS

| | | | |
|---|---|---|---|
| JP | 2006-068113 | | 3/2006 |
| JP | 2008-178481 A | | 8/2008 |
| JP | WO 2008/149904 | * 12/2008 | H04N 9/04 |

OTHER PUBLICATIONS

Japanese Official Action dated Jan. 7, 2014 received from related application JP 2010-065925.

* cited by examiner

FIG. 6
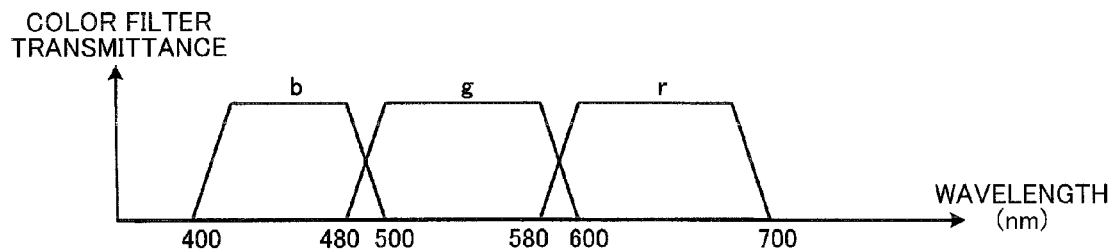
FIG. 7
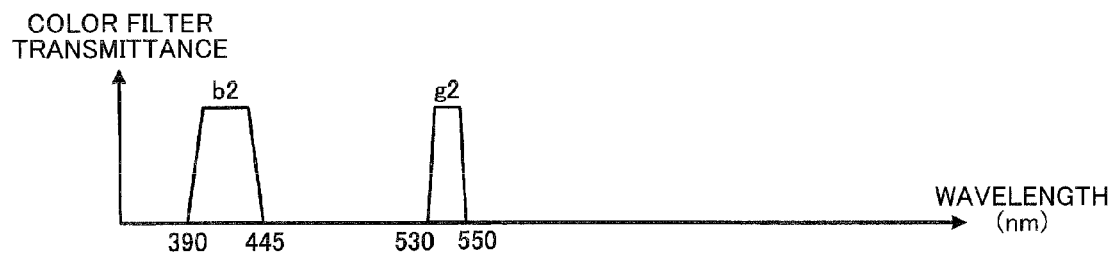
FIG. 8

IMAGE PROCESSING DEVICE, IMAGE PROCESSING METHOD, AND PROGRAM

Japanese Patent Application No. 2010-65925 filed on Mar. 23, 2010, is hereby incorporated by reference in its entirety.

BACKGROUND

The present invention relates to an image processing device, an image processing method, a program, and the like.

A frame sequential endoscope system that sequentially applies three colors of light (R1, G1, and B1) to tissues in a body cavity using a rotary filter, and allows diagnosis using an image (normal light image) generated from the resulting reflected light images, has been widely used. JP-A-2006-68113 discloses an endoscope system that sequentially applies narrow-band light G2 and narrow-band light B2 that differ from the above three colors of light to tissues in a body cavity, and allows diagnosis using a narrow-band light image (special light image) generated from the resulting reflected light images.

When using an endoscope system that acquires a special light image (e.g., JP-A-2006-68113), capillaries and a minute mucous membrane pattern in the mucous membrane surface layer are enhanced (highlighted), so that a lesion area (e.g., epidermoid cancer) that cannot be easily observed using normal light can be easily found.

SUMMARY

According to one aspect of the invention, there is provided an image processing device comprising:
  a normal light image acquisition section that acquires a normal light image that includes an object image and includes information within a wavelength band of white light;
  a special light image acquisition section that acquires a special light image that is generated from reflected narrow-band light that differs from the white light, the special light image including an object image and includes information within a specific wavelength band;
  a correction section that performs a correction process on the special light image; and
  a blending section that performs a blending process that blends the normal light image and a corrected special light image that is the special light image corrected by the correction section,
  the blending section performing at least one of a first blending process that blends a component G of the normal light image and a component G of the corrected special light image, and a second blending process that blends a component B of the normal light image and a component B of the corrected special light image as the blending process.

According to another aspect of the invention, there is provided an image processing device comprising:
  a normal light image acquisition section that acquires a normal light image that includes an object image and includes information within a wavelength band of white light;
  a special light image acquisition section that acquires a special light image that includes an object image and includes information within a specific wavelength band; and
  a correction section that performs a correction process on the special light image based on special light luminance information that is luminance information about the special light image.

According to another aspect of the invention, there is provided an image processing method comprising:
  acquiring a normal light image that includes an object image and includes information within a wavelength band of white light;
  acquiring a special light image that is generated from reflected narrow-band light that differs from the white light, the special light image including an object image and includes information within a specific wavelength band;
  performing a correction process on the special light image; and
  performing at least one of a first blending process that blends a component G of the normal light image and a component G of the corrected special light image, and a second blending process that blends a component B of the normal light image and a component B of the corrected special light image as a blending process that blends the normal light image and the corrected special light image.

According to another aspect of the invention, there is provided an information storage device having stored thereon a program, the program causing a computer to function as:
  a normal light image acquisition section that acquires a normal light image that includes an object image and includes information within a wavelength band of white light;
  a special light image acquisition section that acquires a special light image that is generated from reflected narrow-band light that differs from the white light, the special light image including an object image and includes information within a specific wavelength band;
  a correction section that performs a correction process on the special light image; and
  a blending section that performs a blending process that blends the normal light image and a corrected special light image that is the special light image corrected by the correction section,
  the blending section performing at least one of a first blending process that blends a component G of the normal light image and a component G of the corrected special light image, and a second blending process that blends a component B of the normal light image and a component B of the corrected special light image as the blending process.

According to another aspect of the invention, there is provided a program stored in an information storage medium, the program causing a computer to function as:
  a normal light image acquisition section that acquires a normal light image that includes an object image and includes information within a wavelength band of white light;
  a special light image acquisition section that acquires a special light image that includes an object image and includes information within a specific wavelength band; and
  a correction section that performs a correction process on the special light image based on special light luminance information that is luminance information about the special light image.

BRIEF DESCRIPTION OF THE DRAWINGS

FIG. 6 shows the spectral characteristics of color filters r, g, and b.

FIG. 7 shows the spectral characteristics of color filters g2 and b2.

FIG. 8 is a view illustrative of color filters g2 and b2.

Figures 14A, 14B, 14C, 14D:
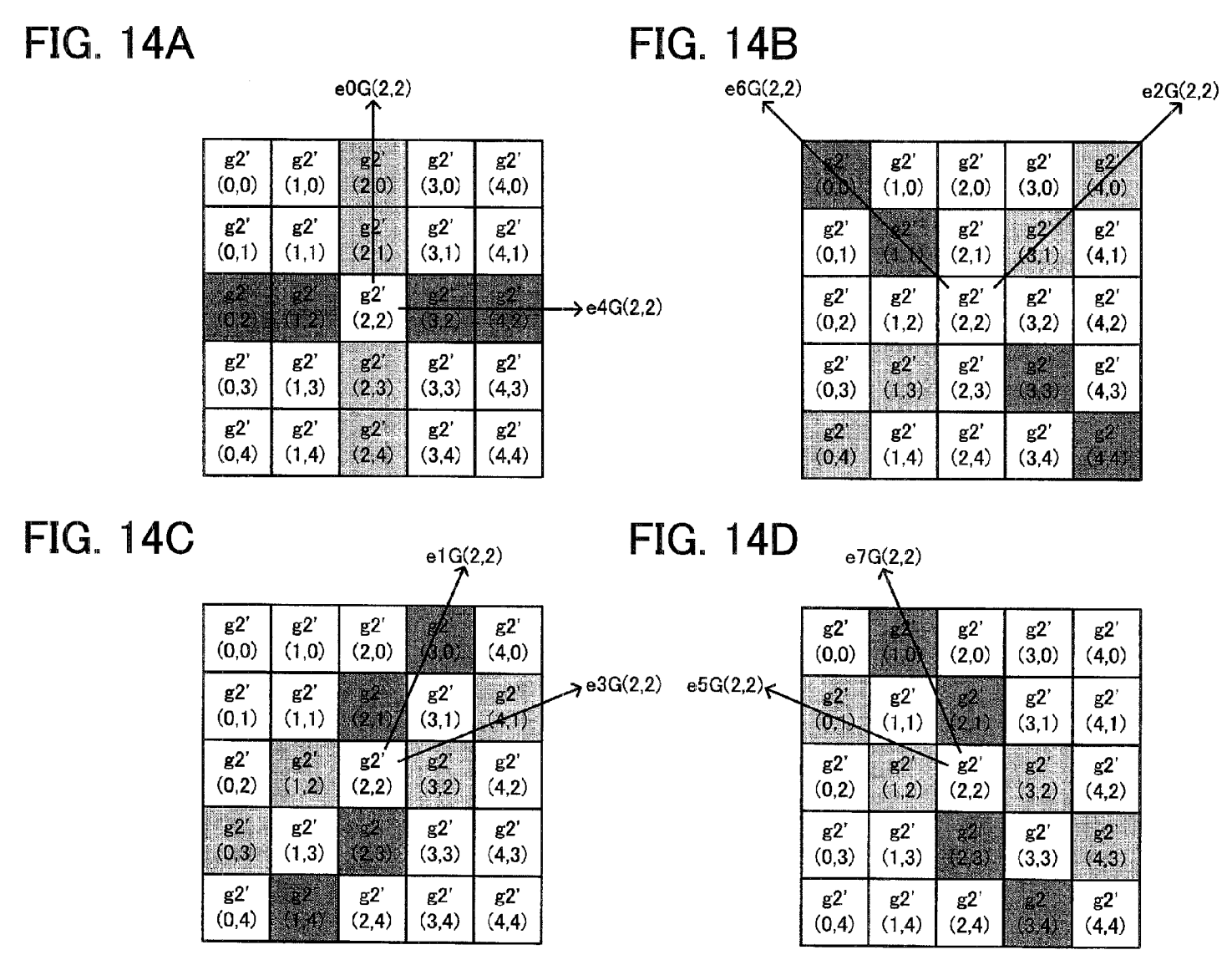

FIGS. 14A to 14D are views illustrative of a pixel and a direction used when determining the edge direction.

DESCRIPTION OF EXEMPLARY EMBODIMENTS

Figure 1A:
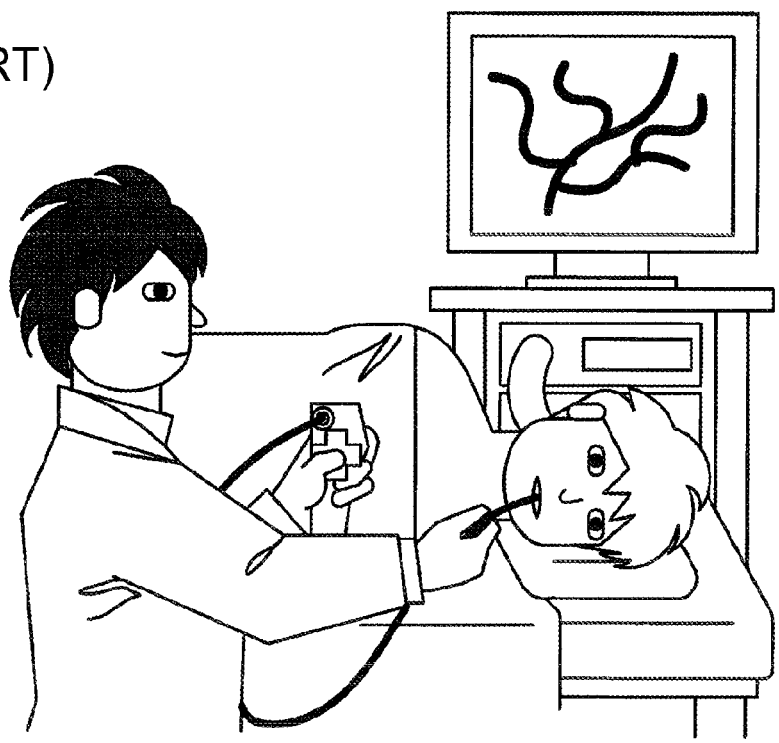
FIGS. 1A and 1B are views illustrative of a related-art method.

Several aspects of the invention may provide an image processing device, an image processing method, a program, and the like that improve the visibility of an object (e.g., blood vessel) as compared with the case of blending a pseudo-color special light image, by acquiring a normal light image corresponding to the wavelength region of normal light and a special light image corresponding to a specific wavelength region, correcting the special light image, and blending the components G and the components B of the corrected special light image and the normal light image.

Several aspects of the invention may provide an image processing device, an image processing method, a program, and the like that prevent a situation in which a lesion area is missed while reducing the burden on the doctor during diagnosis that utilizes a normal light image and a special light image.

According to one embodiment of the invention, there is provided an image processing device comprising:
  a normal light image acquisition section that acquires a normal light image that includes an object image and includes information within a wavelength band of white light;
  a special light image acquisition section that acquires a special light image that is generated from reflected narrow-band light that differs from the white light, the special light image including an object image and includes information within a specific wavelength band;
  a correction section that performs a correction process on the special light image; and
  a blending section that performs a blending process that blends the normal light image and a corrected special light image that is the special light image corrected by the correction section,
  the blending section performing at least one of a first blending process that blends a component G of the normal light image and a component G of the corrected special light image, and a second blending process that blends a component B of the normal light image and a component B of the corrected special light image as the blending process.

According to the above embodiment, the normal light image and the special light image are acquired. The special light image is corrected to acquire a corrected special light image, and the components G and the components B of the corrected special light image and the normal light image are blended. Therefore, the visibility of the object (e.g., blood vessel) can be improved as compared with the case of blending a pseudo-color special light image with the normal light image.

According to another embodiment of the invention, there is provided an image processing device comprising:
  a normal light image acquisition section that acquires a normal light image that includes an object image and includes information within a wavelength band of white light;
  a special light image acquisition section that acquires a special light image that includes an object image and includes information within a specific wavelength band; and
  a correction section that performs a correction process on the special light image based on special light luminance information that is luminance information about the special light image.

According to the above embodiment, the normal light image and the special light image are acquired, and the correction process is performed on the special light image based on the brightness information about the special light image. This makes it possible to obtain a bright special light image as compared with the case where the correction process is not performed, so that the visibility of the image is improved.

According to another embodiment of the invention, there is provided an image processing method comprising:
  acquiring a normal light image that includes an object image and includes information within a wavelength band of white light;
  acquiring a special light image that is generated from reflected narrow-band light that differs from the white light, the special light image including an object image and includes information within a specific wavelength band;
  performing a correction process on the special light image; and
  performing at least one of a first blending process that blends a component G of the normal light image and a component G of the corrected special light image, and a second blending process that blends a component B of the normal light image and a component B of the corrected special light image as a blending process that blends the normal light image and the corrected special light image.

According to another embodiment of the invention, there is provided an information storage device having stored thereon a program, the program causing a computer to function as:
- a normal light image acquisition section that acquires a normal light image that includes an object image and includes information within a wavelength band of white light;
- a special light image acquisition section that acquires a special light image that is generated from reflected narrow-band light that differs from the white light, the special light image including an object image and includes information within a specific wavelength band;
- a correction section that performs a correction process on the special light image; and
- a blending section that performs a blending process that blends the normal light image and a corrected special light image that is the special light image corrected by the correction section,
- the blending section performing at least one of a first blending process that blends a component G of the normal light image and a component G of the corrected special light image, and a second blending process that blends a component B of the normal light image and a component B of the corrected special light image as the blending process.

According to another embodiment of the invention, there is provided a program stored in an information storage medium, the program causing a computer to function as:
- a normal light image acquisition section that acquires a normal light image that includes an object image and includes information within a wavelength band of white light;
- a special light image acquisition section that acquires a special light image that includes an object image and includes information within a specific wavelength band; and
- a correction section that performs a correction process on the special light image based on special light luminance information that is luminance information about the special light image.

Exemplary embodiments of the invention are described below. Note that the following exemplary embodiments do not in any way limit the scope of the invention laid out in the claims. Note that all of the elements of the following exemplary embodiments should not necessarily be taken as essential elements of the invention.

1. Method

A method according to one embodiment of the invention is described below with reference to FIGS. 1A, 1B, and 2.

Figure 1B:
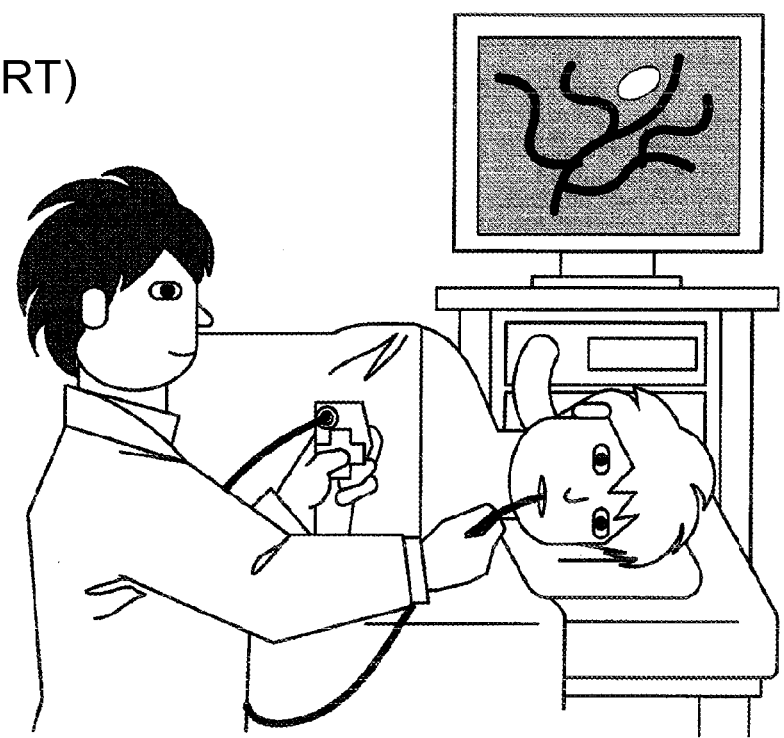

FIGS. 1A and 1B show a related-art method. FIG. 1A shows an observation state using normal light. A bright image that can be easily observed is obtained using normal light. However, it is difficult to observe some lesion such as epidermoid cancer. FIG. 1B shows an observation state using special light (narrow-band light). In this case, the visibility of some lesion can be improved (e.g., some lesion such as epidermoid cancer is displayed in brown) as compared with observation using normal light. However, a dark image that cannot be easily observed is obtained using special light.

In order to solve this problem, diagnosis or treatment may be performed while selectively displaying the normal light image or the special light image by operating a switch of the instrument, for example. According to this method, however, the burden on the doctor increases since it is necessary to operate the instrument and observe the screen while moving the insertion section of the endoscope. Moreover, since each of the normal light image and the special light image has drawbacks, it is necessary to appropriately select the display image depending on the situation. This may require skill.

The normal light image and the special light image may be displayed side by side. In this case, since it is necessary to observe two screens (images) at the same time, the burden on the doctor increases. As a result, a lesion area may be missed, for example.

Figure 2:
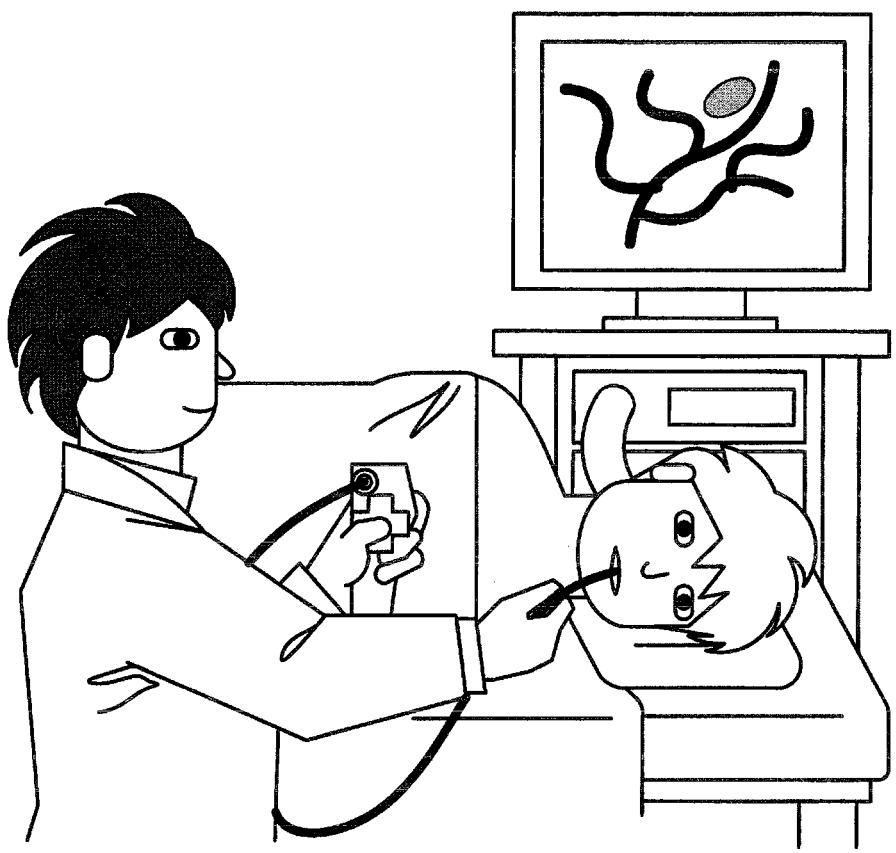
FIG. 2 is a view illustrative of a method according to one embodiment of the invention.

In order to deal with the above problems, this application proposes a system shown in FIG. 2. Specifically, the visibility of a lesion area (e.g., epidermoid cancer) is improved by extracting capillaries and a minute mucous membrane pattern in the mucous membrane surface layer from the special light image, and performing the blending process on the special light image and the normal light image based on the extracted information.

Since the advantage (i.e., visibility of a lesion area) of the special light image is thus added to the advantage (i.e., bright and easily observable) of the normal light image, smooth diagnosis or treatment can be implemented by preventing a situation in which a lesion area is missed, and reducing the burden on the doctor.

Note that the special light image may also be displayed by operating a switch of the instrument, for example. For example, the blended normal light image may be used when searching for a lesion area, and the special light image may be used when observing the details of the lesion area (i.e., the images may be selectively used).

2. First Embodiment

A method according to this embodiment is described below with reference to FIGS. 3 and 4.

Figure 3:
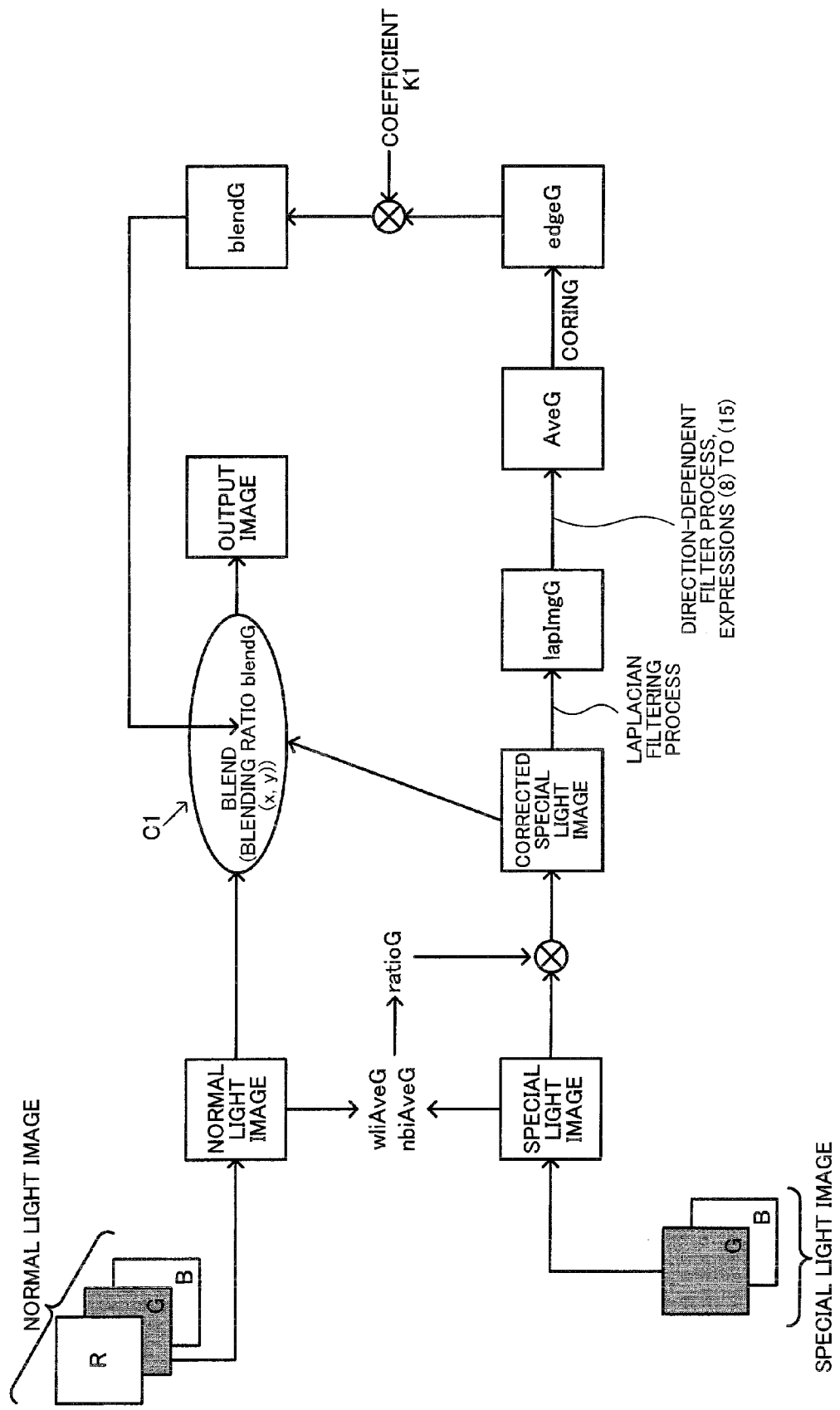
FIG. 3 is a view illustrative of a component G blending process according to one embodiment of the invention.
Figure 4:
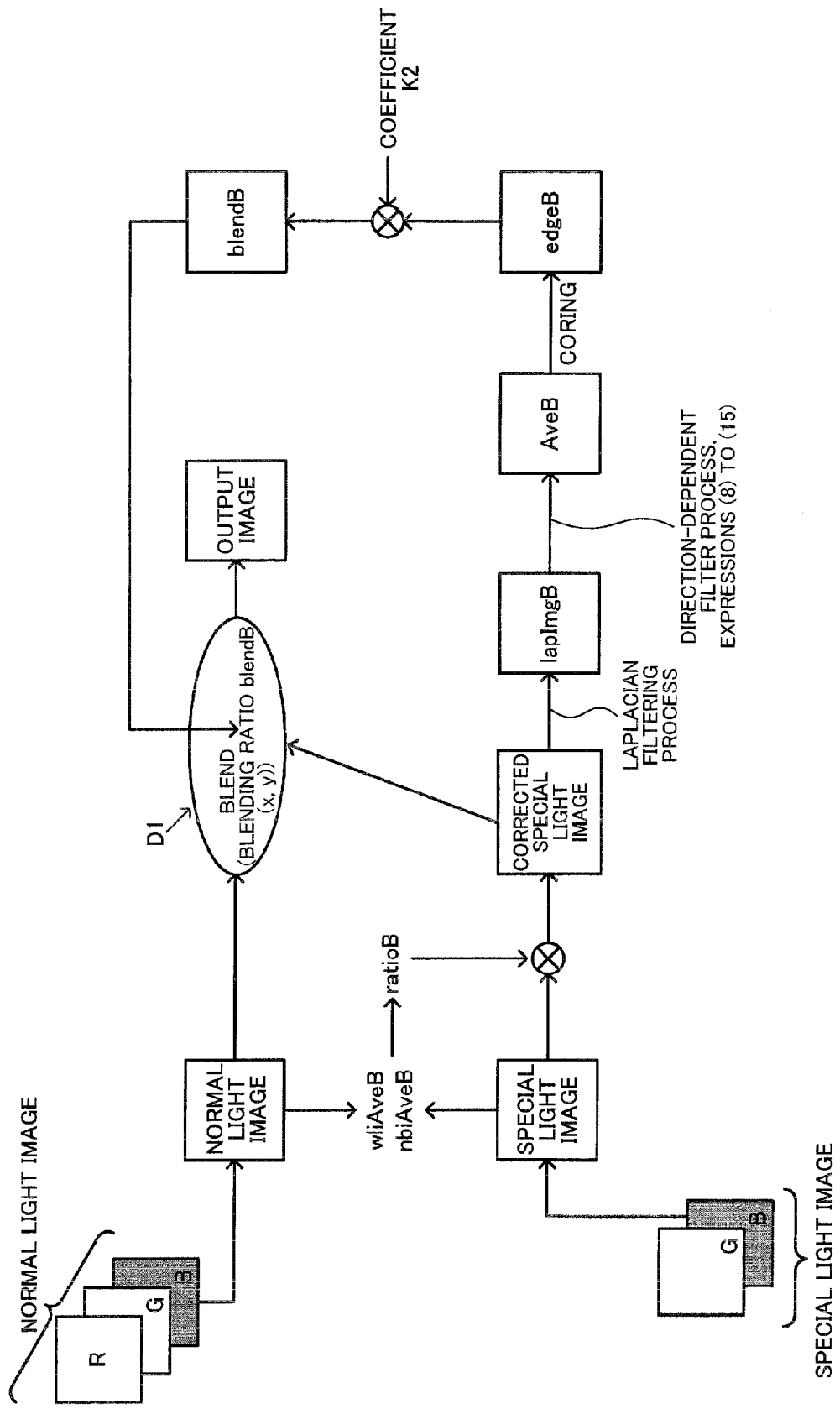
FIG. 4 is a view illustrative of a component B blending process according to one embodiment of the invention.

FIG. 3 is a view illustrative of a component G blending process. The special light image includes components G2 and B2 (when the special light image is an NBI image), and the component G2 is extracted. The normal light image includes components R, G, and B, and the component G that corresponds to the component G2 is extracted.

A ratio ratioG is calculated by the expression (3) (described later) from the ratio of luminance information wliAveG about the component G of the normal light image to luminance information nbiAveG about the component G2 of the special light image. The luminance of the component G2 of the special light image is corrected by the expression (4) (described later) using the ratio ratioG to acquire the corrected special light image (component G).

The corrected special light image and the component G of the normal light image are blended by the expression (24) (described later) using a blending ratio blendG to acquire an output image (component G). Note that the process according to this embodiment aims at acquiring the output image. The blending ratio blendG is calculated the following process.

When calculating the blending ratio blendG, the corrected special light image is subjected to a Laplacian filtering process to acquire an edge image lapImgG. The edge direction in the edge image lapImgG, is determined using the expressions (8) to (15) (described later), and an image AveG is acquired by applying a direction-dependent filtering process that calculates the average value of the pixel values along the edge direction.

The image AveG is subjected to a coring process (expressions (16) to (20) (described later) to acquire an edge information image edgeG. The blending ratio blendG is acquired by multiplying the edge information image edgeG by a coefficient K1, and the blending process is performed on the component G of the normal light image and the corrected special light image using the acquired blending ratio blendG to acquire an output image.

Likewise, the component B2 of the special light image is blended with the component B of the normal light image. FIG. 4 schematically shows a component B blending process.

The component B blending process is performed in the same manner as the component G blending process. Specifically, a ratio ratioB is calculated from the ratio of luminance information about the component B of the normal light image to luminance information about the component B2 of the special light image, and the luminance of the component B2 of the special light image is corrected. The component B of the normal light image and the corrected special light image (component B) are blended using a blending ratio blendB to acquire an output image (component B).

The blending ratio blendB is calculated by subjecting the corrected special light image to the Laplacian filtering process and the direction-dependent filtering process, calculating an edge information image edgeB by performing the coring process, and multiplying the edge information image edgeB by a coefficient K2.

Since the special light image does not include a component corresponding to the channel R, the component R of the normal light image is used as the component R of the output image (expression (23) (described later)).

A color image is generated based on the components R, B, and G of the output image thus obtained. Since the blood vessels and the like are enhanced in a natural color in the generated image, the visibility of the structure (e.g., blood vessels) and a lesion area is improved. This makes it possible to reduce the burden on the doctor during diagnosis, for example.

The system configuration and the above process are described in detail below.

An image processing device according to this embodiment and an endoscope system including the same are described below with reference to FIG. 5. The endoscope system according to this embodiment includes a light source section 100, an insertion section 200, an image processing section 300 that corresponds to the image processing device according to this embodiment, a display section 400, and an external I/F section 500.

The light source section 100 includes a white light source 110 that emits (generates) white light, and a condenser lens 120 that focuses white light on a light guide fiber 210.

The insertion section 200 is formed to be elongated and flexible (i.e., can be curved) so that the insertion section 200 can be inserted into a body cavity or the like. The insertion section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, a half mirror 240 that separates the focused reflected light into two, and a first imaging element 250 and a second imaging element 260 that detect the separated reflected light.

The first imaging element 250 includes a Bayer color filter array that is used to capture the normal light image. Color filters R, G, and B of the first imaging element 250 have spectral characteristics shown in FIG. 6, for example. The second imaging element 260 captures a narrow-band light image. As shown in FIG. 8, the second imaging element 260 has a configuration in which color filters g2 that allow narrow-band light G2 to pass through and color filters b2 that allow narrow-band light B2 to pass through are disposed in a staggered arrangement, for example. As shown in FIG. 7, the color filter g2 of the second imaging element 260 allows light within a wavelength band of 530 to 550 nm to pass through, and the color filter b2 of the second imaging element 260 allows light within a wavelength band of 390 to 445 nm to pass through, for example.

The image processing section 300 (image processing device) includes AD conversion sections 310a and 310b, a normal light image acquisition section 320, a special light image acquisition section 330, an output image generation section 340, a selection section 350, and a control section 360. The control section 360 is bidirectionally connected to the normal light image acquisition section 320, the special light image acquisition section 330, the output image generation section 340, and the selection section 350, and controls the normal light image acquisition section 320, the special light image acquisition section 330, the output image generation section 340, and the selection section 350.

The external I/F section 500 is an interface that allows the user to perform an input operation or the like on the image processing device (endoscope system). The external I/F section 500 includes a power supply switch (power supply ON/OFF switch), a shutter button (photographing start button), a mode (e.g., photographing mode) change button, and the like. The external I/F section 500 outputs input information to the control section 360.

The AD conversion section 310a converts an analog signal output from the first imaging element 250 into a digital signal, and outputs the digital signal. The AD conversion section 310b converts an analog signal output from the second imaging element 260 into a digital signal, and outputs the digital signal.

The normal light image acquisition section 320 acquires the normal light image based on the digital signal output from the AD conversion section 310a, for example. The special light image acquisition section 330 acquires the special light image based on the digital signal output from the AD conversion section 310b, for example. The normal light image acquisition section 320 and the special light image acquisition section 330 are described in detail later.

The normal light image acquired by the normal light image acquisition section 320 and the special light image acquired by the special light image acquisition section 330 are output to the output image generation section 340. The special light color image acquired by the special light image acquisition section 330 is output to the selection section 350. The output image generation section 340 generates one output image from the normal light image and the special light image, and outputs the output image to the selection section 350. The selection section 350 outputs a display image to the display section 400. The output image generation section 340 is described in detail later.

Figure 9:
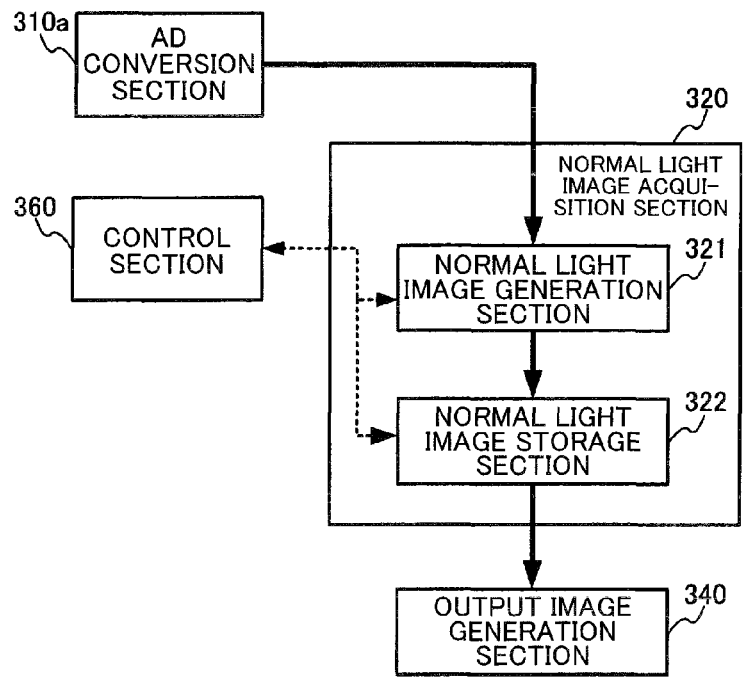
FIG. 9 shows a configuration example of a normal light image acquisition section.

The normal light image acquisition section 320 is described below with reference to FIG. 9. The normal light image acquisition section 320 includes a normal light image generation section 321, and a normal light image storage section 322. The AD conversion section 310a is connected to the normal light image generation section 321. The normal light image generation section 321 is connected to the normal light image storage section 322. The normal light image storage section 322 is connected to the output image generation section 340.

When a digital signal converted by the AD conversion section 310a has been input to the normal light image generation section 321, the normal light image generation section 321 processes the digital signal to generate a normal light image. Specifically, the normal light image generation section 321 performs an interpolation process, a white balance process, a color conversion process, a grayscale transformation process, and the like on the digital signal to generate a normal light image. The R, G, and B signal values at the coordinates (x, y) of the normal light image are indicated by r(x, y), g(x, y), and b(x, y), respectively. The normal light image storage section 322 stores the normal light image output from the normal light image generation section 321. The normal light image stored in the normal light image storage section 322 is output to the output image generation section 340.

Figure 10:
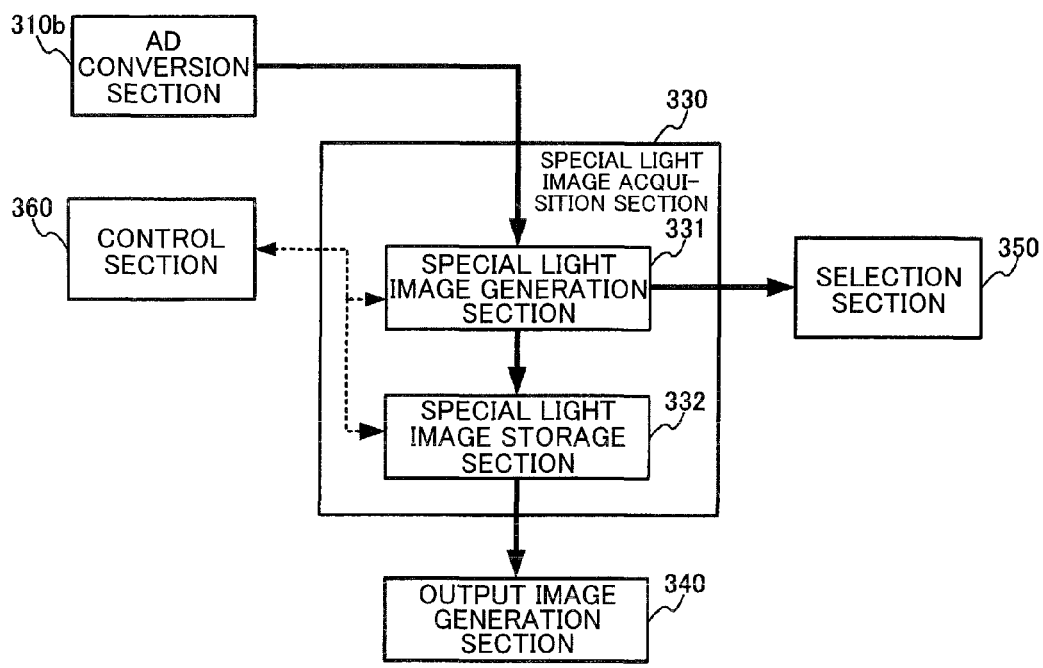
FIG. 10 shows a configuration example of a special light image acquisition section.

The special light image acquisition section 330 is described below with reference to FIG. 10. The special light image acquisition section 330 includes a special light image generation section 331, and a special light image storage section 332. The AD conversion section 310b is connected to the special light image generation section 331. The special light image generation section 331 is connected to the special light image storage section 332 and the selection section 350. The special light image storage section 332 is connected to the output image generation section 340.

When a digital signal converted by the AD conversion section 310b has been input to the special light image generation section 331, the special light image generation section 331 processes the digital signal to generate a special light image.

The special light image generation section 331 generates the special light image as follows. A digital image signal input to the special light image generation section has a configuration in which the color filters g2 and b2 are disposed in a staggered arrangement (see FIG. 8). The special light image generation section 331 performs an interpolation process on the image signal to generate a G2 image in which all of the pixels have a signal value of the filter g2, and a B2 image in which all of the pixels have a signal value of the filter b2. The G and B signal values at the coordinates (x, y) of the special light image are indicated by g2(x, y) and b2(x, y), respectively. The pixel value calculated by the interpolation process may be the average value of the four peripheral pixels, for example. For example, the pixel value b2(1,1) at the position g2(1,1) and the pixel value g2(1,2) at the position b2(1,2) shown in FIG. 8 are calculated by the following expressions (1) and (2).

$$b2(1,1)=[b2(0,1)+b2(1,0)+b2(1,2)+b2(2,1)]/4 \quad (1)$$

$$g2(1,2)=[g2(0,2)+g2(1,1)+g2(1,3)+g2(2,2)]/4 \quad (2)$$

The special light image storage section 332 stores the special light image output from the special light image generation section 331. The special light image stored in the special light image storage section 332 is output to the output image generation section 340.

Figure 11:
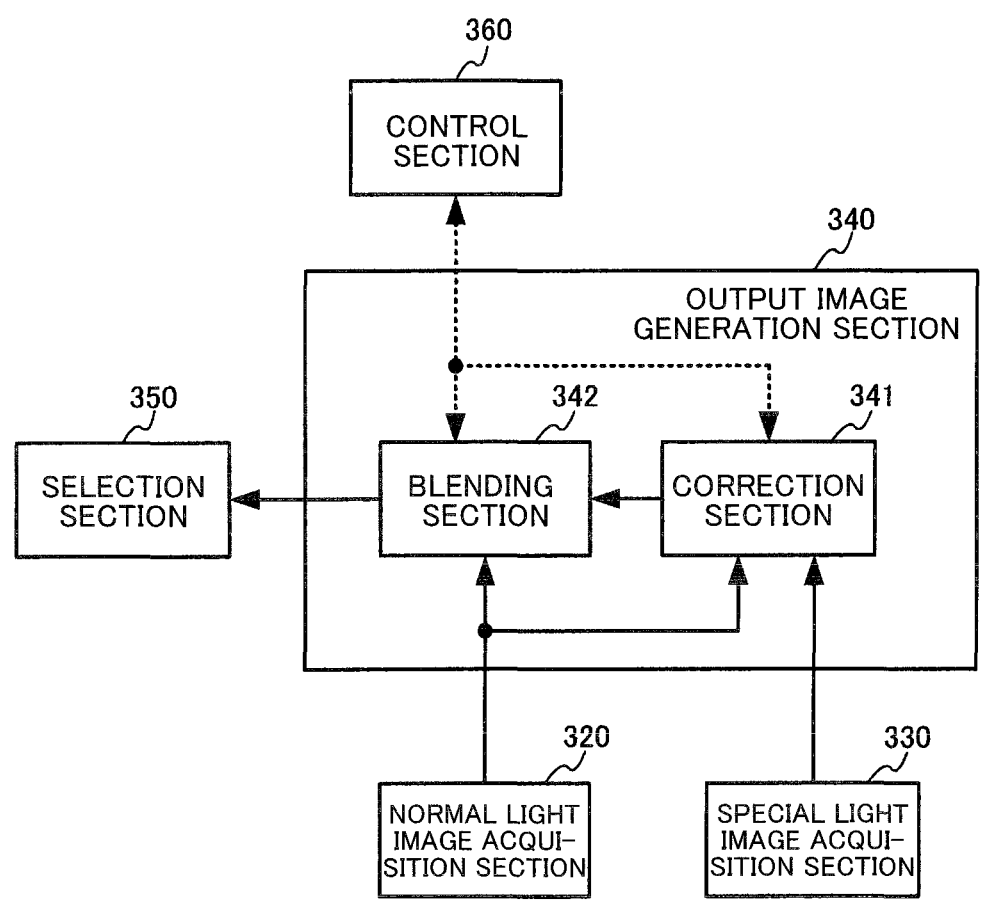
FIG. 11 shows a configuration example of an output image generation section.

A specific configuration of the output image generation section 340 is described below. FIG. 11 is a block diagram illustrative of an example of the configuration of the output image generation section 340 according to the first embodiment. The output image generation section 340 includes a correction section 341 and a blending section 342.

The image signal from the normal light image acquisition section 320 is output to the correction section 341 and the blending section 342. The image signal from the special light image acquisition section 330 is output to the correction section 341. The correction section 341 is connected to the blending section 342. The blending section 342 is connected to the selection section 350. The blending section 342 is described in detail later. The control section 360 is bidirectionally connected to the correction section 341 and the blending section 342, and controls the correction section 341 and the blending section 342.

The correction section 341 performs a correction process on the special light image under control of the control section 360 based on the ratio of the feature quantity of the pixels in the normal light image to the feature quantity of the pixels in the special light image. The term "correction process" used herein refers to a process that corrects the special light image to have a luminance almost equal to that of the normal light image. In this embodiment, the signal G in each image is used as the feature quantity. The average value of the signals G in the special light image is indicated by nbiAveG, and the average value of the signals G in the normal light image is indicated by wliAveG. The ratio ratioG of the signal G of the normal light image to the signal G of the special light image is calculated as follows.

$$\text{ratio}G = K0 \times wliAveG/nbiAveG \quad (3)$$

Note that K0 is a constant term. The signals G and the signals B of all of the pixels of the special light image are multiplied by the signal ratio ratioG. The G and B signals at the coordinates (x, y) of the special light image multiplied by the signal ratio (corrected special light image) are indicated by g2'(x, y) and b2'(x, y), respectively.

$$g2'(x,y)=\text{ratio}G \times g2(x,y) \quad (4)$$

$$b2'(x,y)=\text{ratio}G \times b2(x,y) \quad (5)$$

The signal ratio may be calculated by a method other than the above method. For example, the signal ratio ratioB may be calculated using the average value of the signals B in the special light image and the average value of the signals B in the normal light image, and the signal B in the special light image may be multiplied by the signal ratio ratioB.

$$\text{ratio}B = K0 \times wliAveB/nbiAveB \quad (6)$$

$$b2'(x,y)=\text{ratio}B \times b2(x,y) \quad (7)$$

The image may be divided into a plurality of N×M pixel areas, the average value of each area may be calculated, and the signal ratio of each area may be calculated, for example. The image may be divided into a plurality of areas by applying a known area division algorithm (e.g., texture analysis). The corrected special light image is output to the blending section 342.

Figure 12:
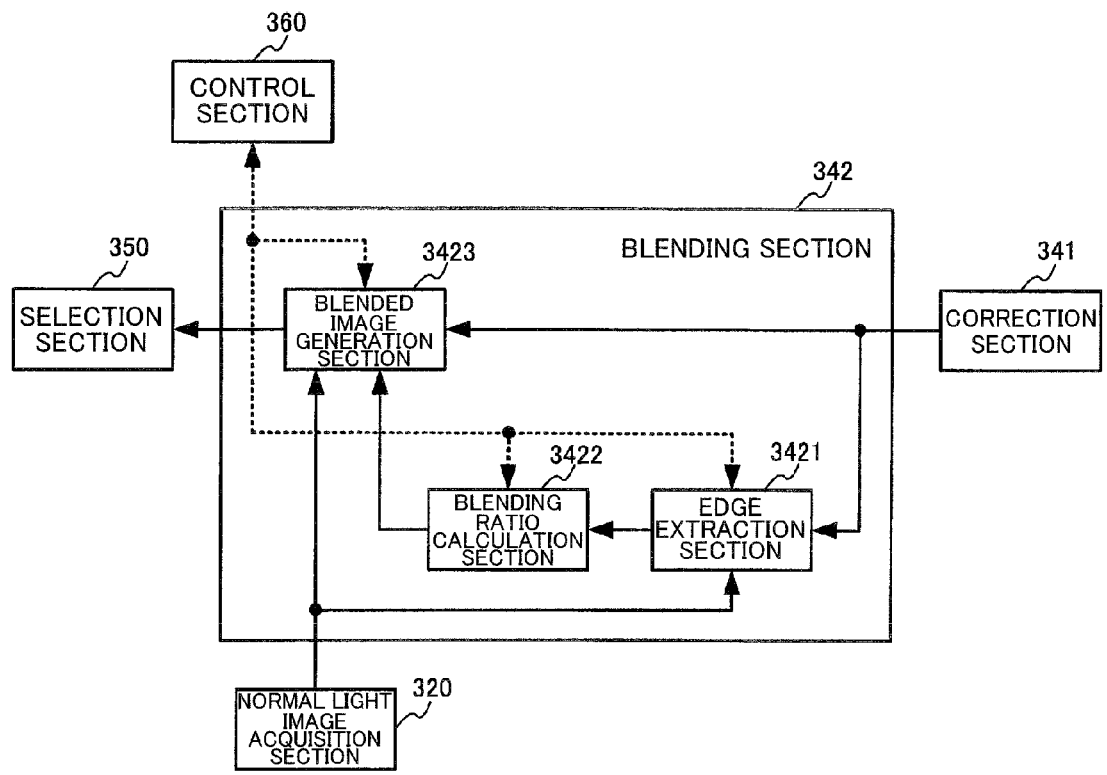
FIG. 12 shows a configuration example of a blending section.

The blending section 342 blends the corrected special light image with the normal light image under control of the control section 360. A specific configuration of the blending section 342 is described below. FIG. 12 is a block diagram illustrative of an example of the configuration of the blending section 342 according to the first embodiment. As shown in FIG. 12, the blending section 342 includes an edge extraction section 3421, a blending ratio calculation section 3422, and a blended image generation section 3423.

The normal light image acquisition section 320 is connected to the edge extraction section 3421 and the blended image generation section 3423. The correction section 341 is connected to the edge extraction section 3421. The edge extraction section 3421 is connected to the blending ratio calculation section 3422. The blending ratio calculation section 3422 is connected to the blended image generation section 3423. The blended image generation section 3423 is connected to the selection section 350. The control section 360 is bidirectionally connected to the edge extraction section 3421, the blending ratio calculation section 3422, and the blended image generation section 3423, and controls the edge extraction section 3421, the blending ratio calculation section 3422, and the blended image generation section 3423.

The edge extraction section 3421 extracts edge information about the corrected special light image and edge information about the normal light image under control of the control section 360. The edge extraction section 3421 performs a direction determination edge extraction process on the G signal value and the B signal value of the special light image.

An example of the direction determination edge extraction process on the G signal value of the special light image is described below. The direction determination edge extraction process is similarly performed on the B signal value of the special light image. Specifically, the signal G of the special light image is subjected to the Laplacian filtering process to generate the edge image lapImgG.

A direction in which an edge component is included is determined from eight directions using all of the pixels of the edge image lapImgG. FIGS. 14A to 14D show a pixel and a direction used when determining the edge direction. Specifically, an evaluation value is calculated using peripheral 5×5 pixels of the attention pixel, and a direction having the minimum evaluation value is used as the determination result. The following expressions (8) to (15) are evaluation expressions when the coordinates of the attention pixel are (2, 2).

$$e0G(2,2)=|g2'(2,2)-g2'(2,3)|+|g2'(2,2)-g2'(2,4)|+|g2'(2,2)-g2'(2,1)|+|g2'(2,2)-g2'(2,0)| \quad (8)$$

$$e1G(2,2)=|g2'(2,2)-g2'(2,3)|+|g2'(2,2)-g2'(1,4)|+|g2'(2,2)-g2'(2,1)|+|g2'(2,2)-g2'(3,0)| \quad (9)$$

$$e2G(2,2)=|g2'(2,2)-g2'(1,3)|+|g2'(2,2)-g2'(0,4)|+|g2'(2,2)-g2'(3,1)|+|g2'(2,2)-g2'(4,0)| \quad (10)$$

$$e3G(2,2)=|g2'(2,2)-g2'(1,2)|+|g2'(2,2)-g2'(0,3)|+|g2'(2,2)-g2'(3,2)|+|g2'(2,2)-g2'(4,1)| \quad (11)$$

$$e4G(2,2)=|g2'(2,2)-g2'(1,2)|+|g2'(2,2)-g2'(0,2)|+|g2'(2,2)-g2'(3,2)|+|g2'(2,2)-g2'(4,2)| \quad (12)$$

$$e5G(2,2)=|g2'(2,2)-g2'(1,2)|+|g2'(2,2)-g2'(0,1)|+|g2'(2,2)-g2'(3,2)|+|g2'(2,2)-g2'(4,3)| \quad (13)$$

$$e6G(2,2)=|g2'(2,2)-g2'(1,1)|+|g2'(2,2)-g2'(0,0)|+|g2'(2,2)-g2'(3,3)|+|g2'(2,2)-g2'(4,4)| \quad (14)$$

$$e7G(2,2)=|g2'(2,2)-g2'(2,1)|+|g2'(2,2)-g2'(1,0)|+|g2'(2,2)-g2'(2,3)|+|g2'(2,2)-g2'(3,4)| \quad (15)$$

The edge image lapImgG generated by the Laplacian filtering process is subjected to a filtering process along the edge direction using the determined result. This reduces noise of the edge image while maintaining the edge. Specifically, the average value AveG(x, y) of the five pixels of the edge image used to calculate the minimum evaluation value using the expressions (8) to (15) is calculated, and used as the output value of the direction-dependent filtering process.

The coring process is then performed on the average value AveG(x, y) calculated by the direction-dependent filtering process so that noise of the edge image and an artifact due to a direction determination error are removed. The coring amount is controlled so that the coring amount is large in the flat area and is small in the edge area.

Specifically, the values e0G(x, y), e2G(x, y), e4G(x, y), and e6G(x, y) calculated by the expressions (8), (10), (12), and (14) are compared, and the maximum value evaMaxG(x, y) is used as the edge amount index. The coring amount evaCoreG (x, y) of each pixel is calculated by the following expressions (16) to (18) using the edge amount index evaMaxG(x, y), a maximum coring amount coreMaxG, a minimum coring amount coreMinG, a slope slopeG, and an edge amount index threshold value TheG (i.e., parameters supplied in advance from the outside).

When the edge amount index evaMaxG is smaller than the threshold value TheG:

$$evaCoreG(x,y)=coreMaxG \quad (16)$$

When the edge amount index evaMaxG is equal to or larger than the threshold value TheG:

$$evaCoreG(x,y)=coreMaxG-((evaMaxG(x,y)-TheG)\times slopeG) \quad (17)$$

When the coring amount evaCoreG is smaller than the minimum coring amount coreMinG:

$$evaCoreG(x,y)=coreMinG \quad (18)$$

The coring process is then performed on the output value AveG(x, y) of the direction-dependent filtering process by the following expressions (19) and (20) using the calculated coring amount evaCoreG(x, y) to calculate the edge information edgeG(x, y).

When the output value AveG (x, y) is equal to or larger than 0:

$$edgeG(x,y)=AveG(x,y)-evaCoreG(x,y) \quad (19)$$

When the edge information edgeG(x, y) has become smaller than 0, 0 is substituted for the edge information edgeG(x, y).

When the output value AveG(x, y) is smaller than 0:

$$edgeG(x,y)=AveG(x,y)+evaCoreG(x,y) \quad (20)$$

When the edge information edgeG(x, y) has become larger than 0, 0 is substituted for the edge information edgeG(x, y).

Note that a known edge extraction method may be used instead of using the direction determination filtering process as the edge information. The edge image edgeG of the G signal value of the special light image and the edge image edgeB of the B signal value of the special light image thus generated are output to the blending ratio calculation section 3422.

The blending ratio calculation section 3422 calculates the blending ratio under control of the control section 360 based on the edge information extracted by the edge extraction section 3421. Specifically, the blending ratio calculation section 3422 calculates the blending ratios blendG and blendB using the following expressions (21) and (22).

$$blendG(x,y)=K1\times edgeG(x,y) \quad (21)$$

$$blendB(x,y)=K2\times edgeB(x,y) \quad (22)$$

Note that K1 and K2 are constant terms. When the blending ratios blendG(x, y) and blendB(x, y) are equal to or larger than 1, 1 is substituted for the blending ratios blendG(x, y) and blendB(x, y). When the blending ratios blendG(x, y) and blendB(x, y) are equal to or smaller than 0, 0 is substituted for the blending ratios blendG(x, y) and blendB(x, y). Note that the blending ratio may be calculated by a method other than the above method. For example, the corrected special light image may be divided into a plurality of areas, the average values edgeAveG and edgeAveB of the edge information of each area may be calculated, and the blending ratio may be calculated using the average value of the edge information. The calculated blending ratios blendG and blendB are output to the blended image generation section 3423.

The blended image generation section 3423 blends the special light image and the normal light image based on the blending ratio calculated by the blending ratio calculation section 3422 under control of the control section 360. Specifically, the signals R, G, and B (R(x, y), G(x, y), and B(x, y)) of the blended image are calculated by the following expressions.

$$R(x,y)=r(x,y) \quad (23)$$

$$G(x,y)=(1-\text{blend}G(x,y))\times g(x,y)+\text{blend}G(x,y)\times g2'(x,y) \quad (24)$$

$$B(x,y)=(1-\text{blend}B(x,y))\times b(x,y)+\text{blend}B(x,y)\times b2'(x,y) \quad (25)$$

The blended image is output to the selection section 350.

The selection section 350 selects the display image under control of the control section 360. In this embodiment, the selection section 350 selects the special light color image or the blended image as the display image based on the photographing mode selected using the external I/F section 500. The selected display image is output to the display section 400.

Figure 13:
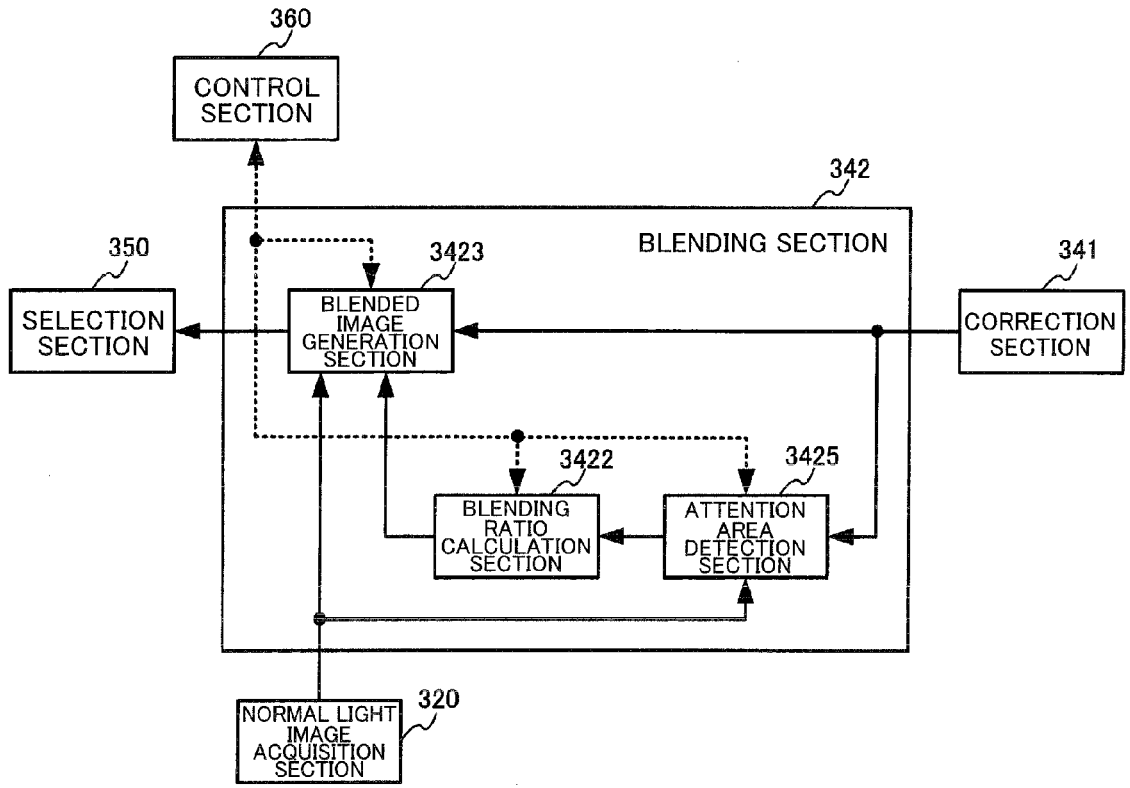
FIG. 13 shows another configuration example of a blending section.

Note that the configuration of the blending section 342 is not limited to the above configuration. For example, the blending section 342 may include an attention area detection section 3425, the blending ratio calculation section 3422, and the blended image generation section 3423, as shown in FIG. 13.

The attention area detection section 3425 detects an attention area. The attention area is not limited to the edge information (e.g., blood vessel), but may be a lesion area or the like. The blending ratio calculation section 3422 increases the blending ratio of the corrected special light image in an area where the attention area has been detected, and decreases the blending ratio of the corrected special light image in an area where the attention area has not been detected.

When performing NBI observation, for example, the components G2 and B2 are input to given channels among the channels R, G, and B to generate a pseudo-color image, so that a specific lesion (e.g., epidermoid cancer) is displayed in brown. Therefore, a brown area (e.g., an area having a hue H of 5 to 35) can be recognized as a lesion area, and detected as the attention area.

Note that the blending method is performed using the expressions (23) to (25). Specifically, the normal light image and the pseudo-color special light image (having the components R, G, and B) are not blended, but the component G of the normal light image and the component G2 of the special light image, and the component B of the normal light image and the component B2 of the special light image, are blended.

The reliability of the attention area may be determined, and the blending ratio of the corrected special light image may be increased as the reliability increases. The area of the brown area (lesion area) may be used as the reliability, for example.

In this embodiment, each section of the image processing section 300 is implemented by hardware. Note that the configuration of the image processing section 300 is not limited thereto. For example, a CPU may perform the process of each section on an image acquired using an imaging apparatus such as a capsule endoscope. Specifically, the process of each section may be implemented by software by causing the CPU to execute a program. Alternatively, part of the process of each section may be implemented by means of software.

When separately providing the imaging section and the AD conversion section, and implementing the process of each section of the image processing section 300 other than the AD conversion section by means of software, a known computer system (e.g., work station or personal computer) may be used as the image processing device. A program (image processing program) that implements the process of each section of the image processing section 300 may be provided in advance, and executed by the CPU of the computer system.

Figure 15:
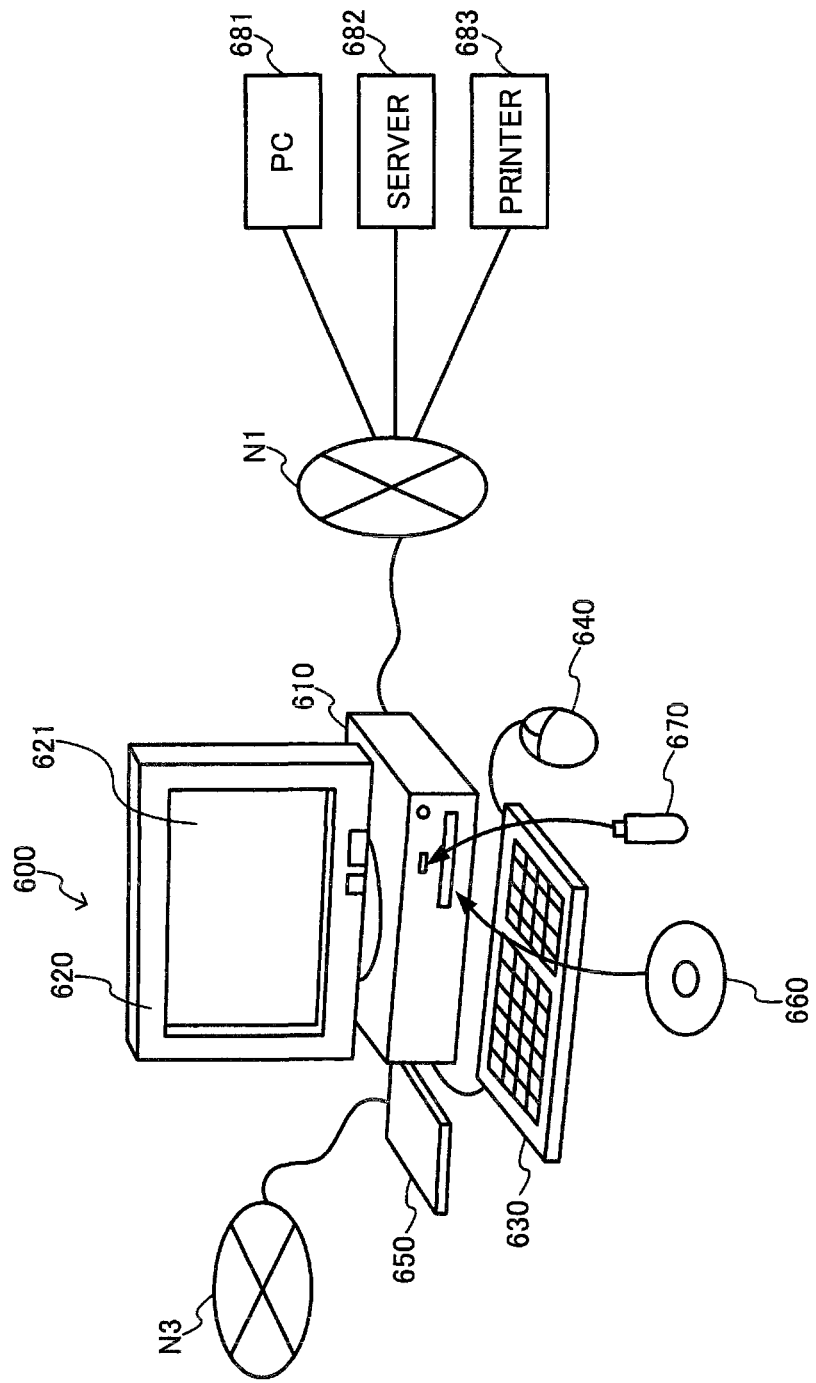
FIG. 15 shows a configuration example of a computer used for a software process.
Figure 16:
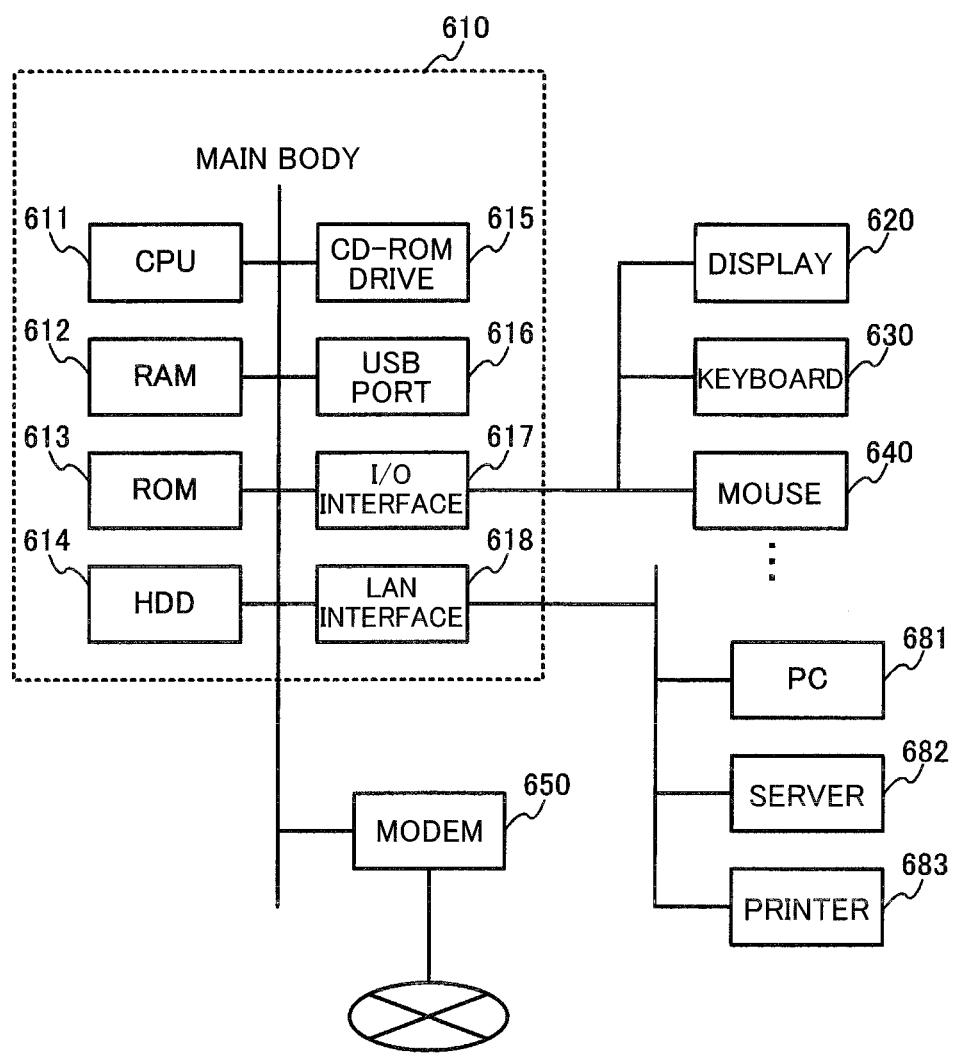
FIG. 16 shows a configuration example of a computer used for a software process.

FIG. 15 is a system configuration diagram showing the configuration of a computer system 600 according to this modification. FIG. 16 is a block diagram showing the configuration of a main body 610 of the computer system 600. As shown in FIG. 15, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As shown in FIG. 16, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to personal computer (PC) 681 (i.e., another computer system), a server 682, a printer 683, and the like via the LAN interface 618 and the local area network or the large area network N1.

The computer system 600 implements the functions of the image processing device by reading an image processing program (e.g., an image processing program that implements a process described later referring to FIGS. 17 and 18) recorded on a given recording medium, and executing the image processing program. The given recording medium may be an arbitrary recording medium that records the image processing program that can be read by the computer system 600, such as the CD-ROM 660, the USB memory 670, a portable physical medium (e.g., MO disk, DVD disk, flexible disk (FD), magnetooptical disk, or IC card), a stationary physical medium (e.g., HDD 614, RAM 612, or ROM 613) that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the image processing program is recorded on a recording medium (e.g., portable physical medium, stationary physical medium, or communication medium) so that the image processing program can be read by a computer. The computer system 600 implements the functions of the image processing device by reading the image processing program from such a recording medium, and executing the image processing program. Note that the image processing program need not necessarily be executed by the computer system 600. The invention may be similarly applied to the case where the computer system (PC) 681 or the server 682 executes the image processing program, or the computer system (PC) 681 and the server 682 execute the image processing program in cooperation.

A process performed when implementing the process of the output image generation section 340 shown in FIG. 11 by software on the normal light image and the special light image acquired in advance is described below using a flowchart shown in FIG. 17 as an example of implementing part of the process of each section by software.

Specifically, header information (e.g., photographing mode) is input to the time-series normal light image and the special light image (S11). The special light image and the normal light image are input to an image buffer allocated in advance (S12). An interpolation process, a white balance process, a color conversion process, a grayscale transformation process, and the like are performed on the input normal light image to generate a normal light image (S13).

The input special light image is processed using the expressions (1) and (2) to generate a special light image (S14). The correction process is performed on the special light image based on the ratio of the feature quantity of the pixels in the normal light image to the feature quantity of the pixels in the special light image (see the expressions (3) to (5)) (S15). The corrected special light image is then blended with the normal light image (described in detail later with reference to FIG. 18) (S16). The image signal subjected to the blending process is then output (S17). Whether or not the process has been performed on the final time-series image is then determined (S18). When it has been determined that the process has not been performed on the final image, the above process is performed on the next image signal from the step S12. When it has been determined that the process has been performed on all of the image signals, the process is terminated.

Figure 17:
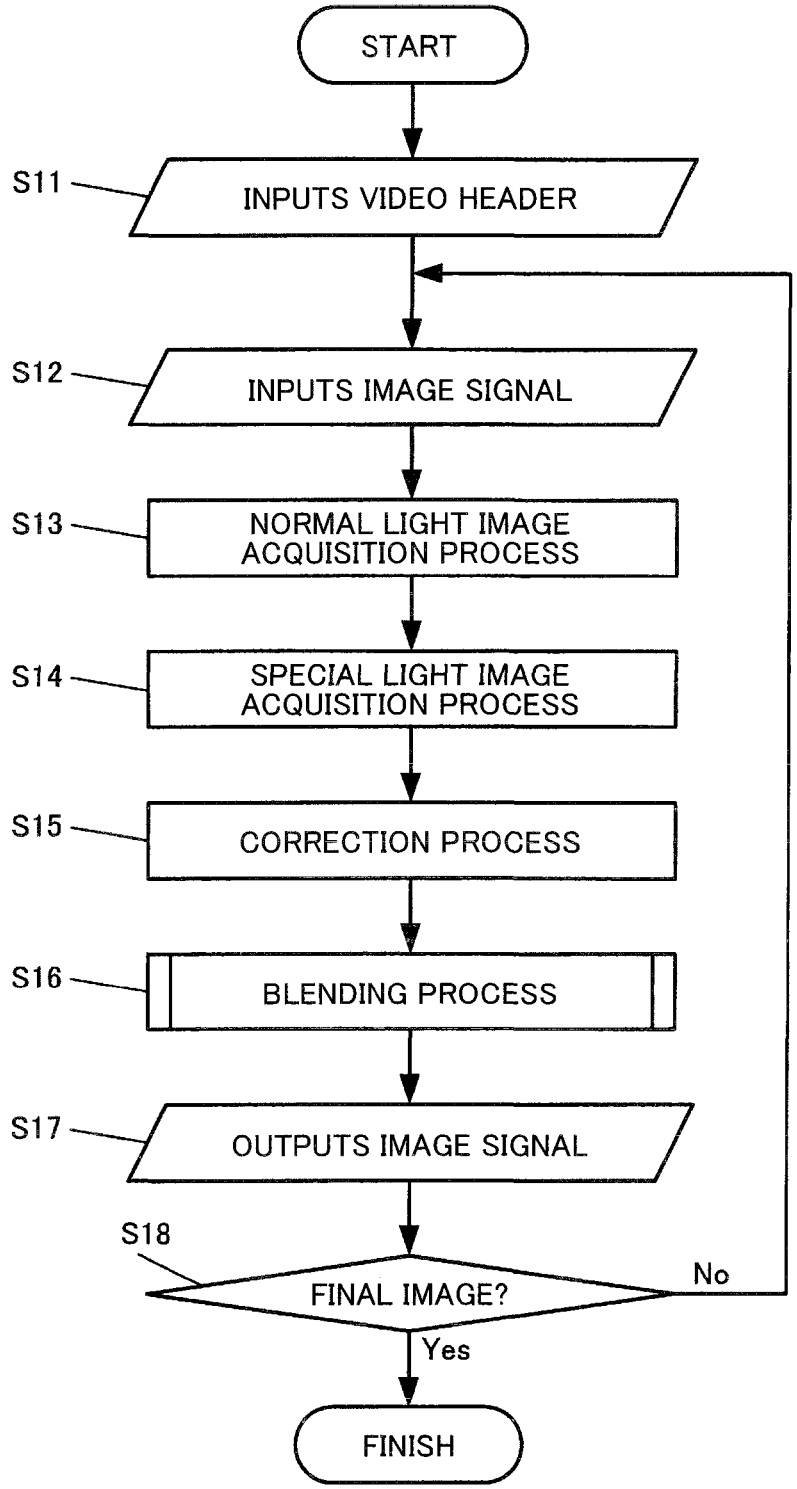
FIG. 17 is a flowchart illustrative of a process according to one embodiment of the invention.
Figure 18:
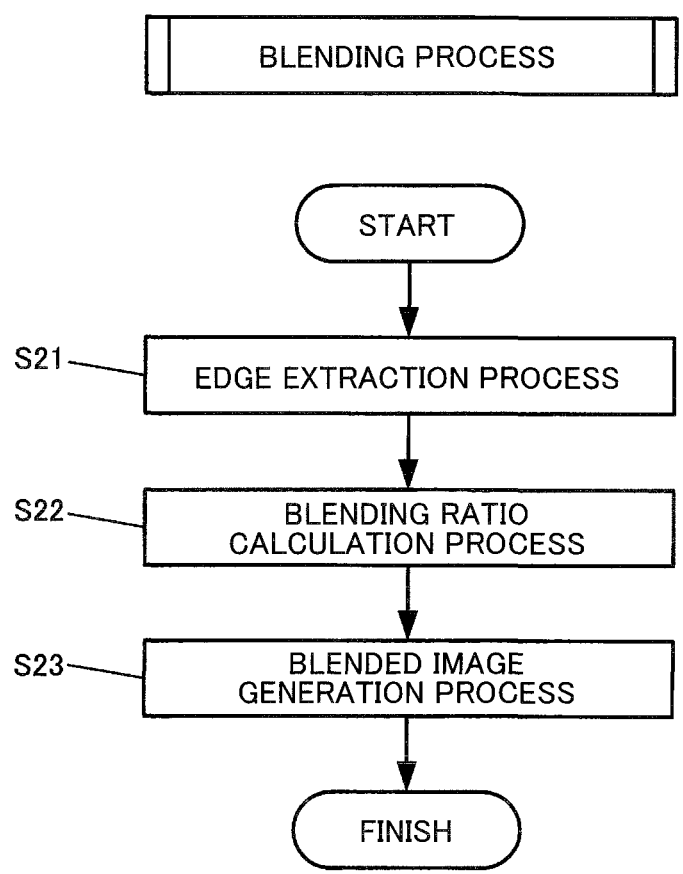
FIG. 18 is a flowchart illustrative of a blending process.

The details of the blending process performed in the step S16 in FIG. 17 are described below with reference to FIG. 18. Specifically, the edge information about the corrected special light image is extracted using the expressions (8) to (20) (S21). The blending ratio is calculated based on the extracted edge information using the expressions (21) and (22) (S22). A blended image is then generated by blending the signals B and G of the normal light image with the signals B and G of the special light image using the expressions (23) to (25) (S23).

The above process makes it possible to display the normal light image and the special light image as a single image. Therefore, it is possible to provide an image processing device (endoscope system) and the like that prevent a situation in which a lesion area is missed while reducing the burden on the doctor.

Figure 5:
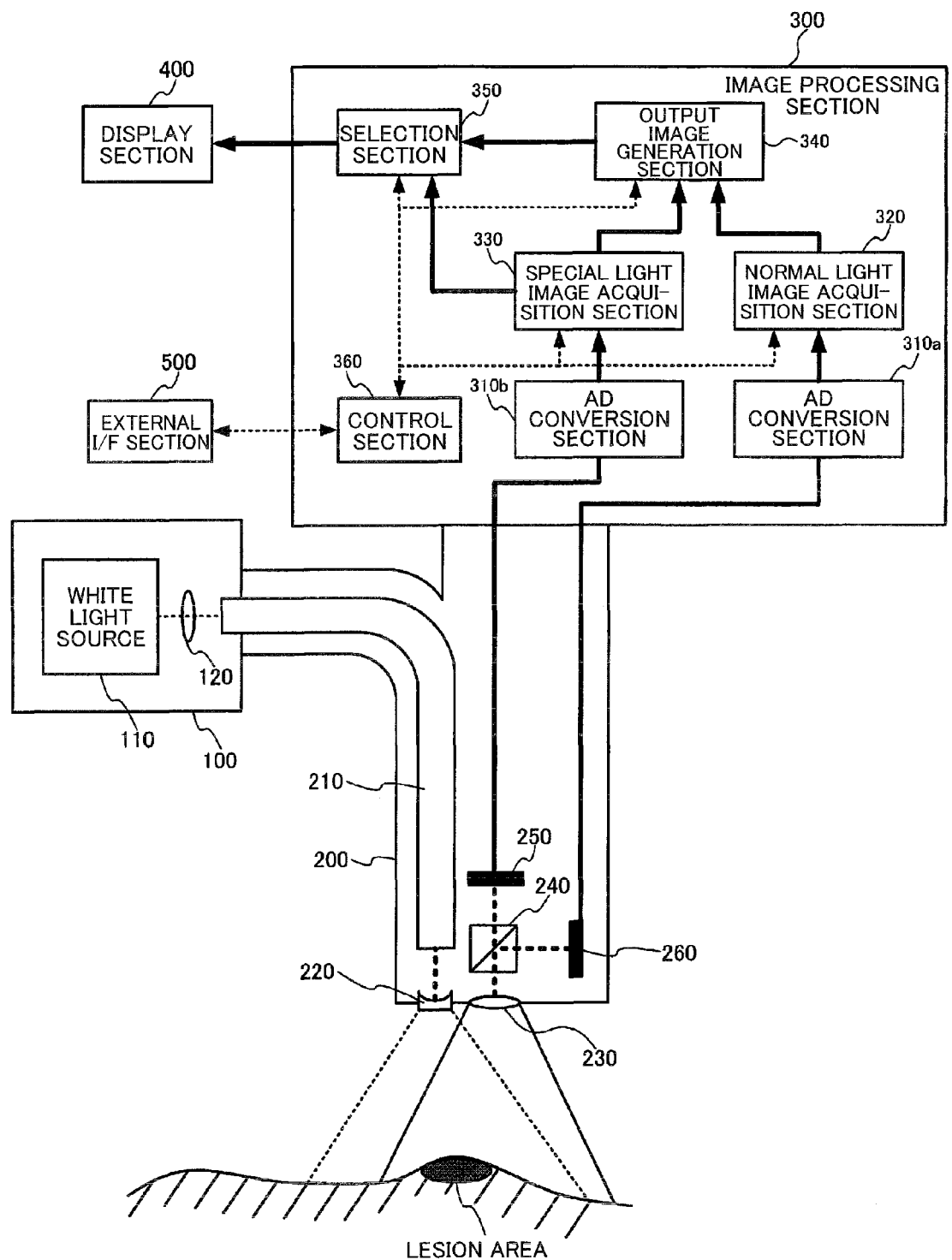
FIG. 5 shows a system configuration example according to one embodiment of the invention.

According to this embodiment, the normal light image acquisition section 320 shown in FIG. 5 acquires an image that includes an object image and includes information within the wavelength band of white light, and the special light image acquisition section 330 acquires an image that includes an object image and includes information within a specific wavelength band. The correction section 341 shown in FIG. 11 performs the correction process on the special light image, and the blending section 342 performs the blending process on the corrected special light image and the normal light image (blending process). Note that the blending process refers to at least one of a first blending process that blends the component G of the normal light image and the component G of the corrected special light image (C1 in FIG. 3), and a second blending process that blends the component B of the normal light image and the component B of the corrected special light image (D1 in FIG. 4).

The term "component" refers to data of each of the channels R, G, and B (i.e., an output when the AD conversion section has converted an analog signal into a digital signal).

An image in which the visibility of capillaries and a minute mucous membrane pattern in the mucous membrane surface layer is higher than that of the normal light image can be obtained by blending the special light image corrected by the correction section 341 with the normal light image. Since the components G and the components B are respectively blended (see C1 in FIG. 3 and D1 in FIG. 4), the visibility of the blood vessels and the like can be improved with a natural color. Therefore, when observing tissues using an endoscope by utilizing normal light and special light, for example, it is possible to allow a lesion area that cannot be easily detected using normal light to be accurately detected using special light, and display an image including the lesion area so that the visibility is higher than that in the case where the method according to this embodiment is not used. Therefore, the burden on the doctor can be reduced while preventing a situation in which the lesion area is missed.

An example in which the components G and the components B are respectively blended has been described above. Note that another configuration may be employed. Specifically, only the components G may be blended without blending the components B, or only the components B may be blended without blending the components G.

As shown in FIG. 12, the blending section 342 may include the edge extraction section 3421 and the blending ratio calculation section 3422. The edge extraction section 3421 may extract at least one of the edge information about the corrected special light image and the edge information about the normal light image, and the blending ratio calculation section 3422 may calculate the blending ratio based on the extracted edge information. The blending section 342 may perform the blending process based on the calculated blending ratio.

The edge information is the edge information image edgeG shown in FIG. 3, and the blending ratio is the blending ratio blendG calculated by multiplying the edge information image edgeG by the coefficient K1 (see the expression (21)). As shown in FIG. 3, the edge information image edgeG is obtained by subjecting the corrected special light image to the Laplacian filtering process, the direction-dependent filtering process, and the coring process.

The edge information is an index that indicates capillaries and a minute mucous membrane pattern in the mucous membrane surface layer included in the special light image.

Specifically, the visibility of the lesion area can be improved as compared with the case of using only normal light by improving the visibility of the lesion area with regard to the pixels of the special light image that include capillaries and a minute mucous membrane pattern in the mucous membrane surface layer, and displaying the pixels that do not include capillaries and a minute mucous membrane pattern in the mucous membrane surface layer using the normal light image. This makes it possible to reduce the burden on the doctor while preventing a situation in which the lesion area is missed.

The blending ratio calculation section 3422 may increase the blending ratio of the corrected special light image when the amount of edges included in the corrected special light image is large as compared with the blending ratio of the corrected special light image when the amount of edges included in the corrected special light image is small. Specifically, the blending ratio of the corrected special light image is increased as the value edgeG increases. This is clear from the expressions (21) and (24). Specifically, the blending ratio blendG of the corrected special light image (see the expression (24)) is determined by the value edgeG (see the expression (21)).

This makes it possible to improve the visibility of the lesion area by increasing the ratio of the special light image in an area that includes capillaries and a minute mucous membrane pattern in the mucous membrane surface layer in a high ratio. Moreover, the visibility of an area that includes capillaries and a minute mucous membrane pattern in the mucous membrane surface layer in a low ratio can be improved by increasing the ratio of the bright normal light image that contains a small amount of noise. This makes it possible to reduce the burden on the doctor while preventing a situation in which the lesion area is missed.

The edge extraction section 3421 shown in FIG. 12 extracts the edge information about the corrected special light image by performing the edge detection filtering process including at least the direction-dependent filtering process on the corrected special light image. For example, the edge extraction section 3421 extracts the edge information about the corrected special light image by performing the Laplacian filtering process and the direction-dependent filtering process on the corrected special light image. This process corresponds to the lapImgG/AveG calculation process shown in FIG. 3.

The direction-dependent filtering process may be a filtering process that smoothes the pixel values of the pixels positioned along the edge direction. Specifically, the edge direction is determined based on the expressions (8) to (15) from the eight directions shown in FIGS. 14A to 14D.

The edge information can be extracted by performing the edge detection filtering process including the direction-dependent filtering process. For example, the edge image can be acquired by performing the Laplacian filtering process, and noise can be reduced by performing the direction-dependent filtering process. Therefore, an image having a sharp edge can be acquired as the edge information about the corrected special light image.

The edge extraction section 3421 may extract the edge information about the normal light image by performing the Laplacian filtering process and the direction-dependent filtering process on the normal light image. This process corresponds to the lapImgY/AveY calculation process shown in FIG. 19.

For example, the edge image can be acquired by performing the Laplacian filtering process, and noise can be reduced by performing the direction-dependent filtering process. Therefore, an image having a sharp edge can be acquired as the edge information about the normal light image.

The blending section 342 may include the attention area detection section 3425 and the blending ratio calculation section 3422, as shown in FIG. 13. The attention area detection section 3425 may detect the attention area within the corrected special light image, and the blending ratio calculation section 3422 may calculate the blending ratio based on the detected attention area information. The blending section 342 may perform the blending process based on the calculated blending ratio. For example, the attention area is detected by generating a pseudo-color image from the signals G2 and B2 of the special light image, and determining the hue H.

The visibility of the lesion area can be improved as compared with the case of using only normal light by improving the visibility of the attention area (e.g., lesion area) within the special light image, and displaying the pixels other than the attention area using the normal light image.

The blending ratio calculation section 3422 shown in FIG. 13 may increase the blending ratio of the corrected special light image when the attention area has been detected as compared with the case where the attention area has not been detected.

This makes it possible to improve the visibility of the lesion area or the like as a result of increasing the ratio of the special light image in the attention area. Moreover, the visibility of an area other than the attention area is improved since the ratio of the bright normal light image that contains a small amount of noise increases.

The blending section 342 may include a division section that divides the corrected special light image into a plurality of areas. The blending ratio calculation section 3422 may calculate the blending ratio in each of the plurality of areas.

This makes it possible to perform the process in units of areas including a plurality of pixels. Therefore, the amount of calculations can be reduced, so that the processing speed can be increased. Moreover, the blending ratio does not change to a large extent depending on the pixel as compared with the case where the corrected special light image is not divided into a plurality of areas, and an artifact does not occur even when a pixel that includes capillaries and a minute mucous membrane pattern in the mucous membrane surface layer is adjacent to a pixel that does not include capillaries and a minute mucous membrane pattern in the mucous membrane surface layer. This makes it possible to improve the visibility of the lesion area, so that the burden on the doctor can be reduced while preventing a situation in which the lesion area is missed.

The term "specific wavelength band" may be a band that is narrower than the wavelength band of white light. Specifically, the normal light image and the special light image may be in vivo images, and the specific wavelength band may be the wavelength band of a wavelength absorbed by hemoglobin in blood, for example. More specifically, the specific wavelength band may be 390 to 445 nm or 530 to 550 nm (see FIG. 7).

This makes it possible to observe the structure of a surface area of tissues and a blood vessel located in a deep area. A lesion area (e.g., epidermoid cancer) that cannot be easily observed using normal light can be displayed as a brown area or the like by inputting the resulting signal to a given channel (R, G, or B), so that the lesion area can be reliably detected (i.e., a situation in which the lesion area is missed can be prevented). A wavelength band of 390 to 445 nm or 530 to 550 nm is selected from the viewpoint of absorption by hemoglobin and the ability to reach a surface area or a deep area of tissues.

As shown in FIGS. 5 and 11, the image processing device according to this embodiment may include the normal light image acquisition section 320, the special light image acquisition section 330, and the correction section 341. The normal light image acquisition section 320 may acquire an image that includes an object image and includes information within the wavelength band of white light, and the special light image acquisition section 330 may acquire an image that includes an object image and includes information within a specific wavelength band. The correction section 341 may perform the correction process on the special light image based on special light luminance information that is the luminance information about the special light image. The special light luminance information corresponds to the luminance information nbiAveG shown in FIG. 3.

This makes it possible to correct the luminance of the special light image using the special light luminance information. Since the special light image is normally very dark, the visibility of the image can be improved by correcting the luminance.

The correction section 341 shown in FIG. 11 may perform the correction process on the special light image using the special light luminance information and normal light luminance information that is the luminance information about the normal light image. The normal light luminance information corresponds to the luminance information wliAveG shown in FIG. 3.

This makes it possible to correct the luminance of the special light image after comparing the luminance of the normal light image with the luminance of the special light image.

The correction section 341 may cause the special light luminance information to be equal to the normal light luminance information.

This makes it possible to increase the luminance of a very dark special light image to be equal to the luminance of the normal light image, so that the visibility of the image can be improved.

The correction section 341 may perform the correction process on the special light image using the special light luminance information and luminance information obtained from a luminance sensor.

The luminance sensor (light control sensor) is implemented by a photodiode or the like, and operates due to photoelectromotive force, photoconduction, or the like to detect the luminance.

This makes it possible to acquire the luminance information as sensor information, and correct the luminance based on the sensor information.

The correction section 341 may perform the correction process on the special light image based on the pixel value within the special light image and the pixel value within the normal light image.

This makes it possible to implement the correction process based on the pixel value. When 8 bits are assigned to R, G, and B of each pixel, the pixel value is a value of 0 to 255 corresponding to each of the components R, G, and B.

The correction section 341 may calculate the special light luminance information based on the pixel value within the special light image, and may calculate the normal light luminance information based on the pixel value within the normal light image. The correction section 341 may perform the correction process on the special light image based on the special light luminance information and the normal light luminance information. The special light luminance information corresponds to the luminance information nbiAveG shown in FIG. 3, and the normal light luminance information corresponds to the luminance information wliAveG shown in FIG. 3, as described above.

This makes it possible to calculate the luminance information based on the pixel value. The luminance of the special light image can be corrected after comparing the luminance of the normal light image with the luminance of the special light image.

The correction section 341 may calculate a value corresponding to the ratio of the special light luminance information to the normal light luminance information as a correction coefficient, and may multiply the pixel value within the special light image by the correction coefficient. For example, the process based on the expressions (3) and (4) may be employed.

This makes it possible to implement the correction process using the ratio of the special light luminance information to the normal light luminance information (or a value corresponding to the ratio of the special light luminance information to the normal light luminance information) as the correction coefficient.

The normal light image may include first to Nth pixel-value components (e.g., components R, G, and B), and the special light image may include first to Mth pixel-value components (e.g., components G2 and B2). The correction section 341 may calculate the special light luminance information based on at least one of the first to Mth components. The correction section 341 may calculate the normal light luminance information based on the component of the normal light image corresponding to the component used to calculate the special light luminance information. For example, the component of the normal light image corresponding to the component used to calculate the special light luminance information may be at least one of the components G and B. As shown in FIG. 3, when the signal G2 has been used to calculate the special light luminance information, the component G corresponds to the component used to calculate the special light luminance information.

This makes it possible to calculate the special light luminance information based on at least one of the pixel-value components of the special light image. Moreover, the normal light luminance information can be calculated based on the pixel-value component of the normal light image corresponding to the pixel-value component of the special light image used to calculate the special light luminance information. When the component G2 has been used to calculate the special light luminance information, the component G of the normal light image is used to calculate the normal light luminance information. When the component B2 has been used to calculate the special light luminance information, the component B of the normal light image is used to calculate the normal light luminance information.

The correction section 341 may calculate the special light luminance information based on the component G (component G2) of the special light image, and may calculate the normal light luminance information based on the component G of the normal light image. The correction section 341 may perform the correction process based on the special light luminance information and the normal light luminance information. Specifically, the correction section 341 may calculate a value corresponding to the ratio of the special light luminance information to the normal light luminance information as a correction coefficient, and may multiply the components G and B of the special light image by the correction coefficient. For example, the process based on the expressions (3) to (5) may be employed.

This makes it possible to increase the luminance of the special light image to be almost equal to the luminance of the normal light image using the signal G with the highest relative luminous efficiency. This makes it possible to improve the visibility of the lesion area, so that the burden on the doctor can be reduced while preventing a situation in which the lesion area is missed.

The correction section 341 may calculate first special light luminance information based on the component G (component G2) of the special light image, and may calculate first normal light luminance information based on the component G of the normal light image. The correction section 341 may calculate second special light luminance information based on the component B (component B2) of the special light image, and may calculate second normal light luminance information based on the component B of the normal light image. The correction section 341 may perform the correction process based on the first special light luminance information, the first normal light luminance information, the second special light luminance information, and the second normal light luminance information.

Specifically, the correction section 341 may calculate a value corresponding to the ratio of the first special light luminance information to the first normal light luminance information as a first correction coefficient, and may multiply the component G of the special light image by the first correction coefficient. The correction section 341 may calculate a value corresponding to the ratio of the second special light luminance information to the second normal light luminance information as a second correction coefficient, and may multiply the component B of the special light image by the second correction coefficient. For example, the process based on the expressions (3), (4), (6), and (7) may be employed.

This makes it possible to optimally correct the luminance individually using the signals G and B. Therefore, the visibility of the lesion area can be improved, so that the burden on the doctor can be reduced while preventing a situation in which the lesion area is missed.

The blending section 342 may blend the component G of the normal light image and the component G of the corrected special light image, and blend the component B of the normal light image and the component B of the corrected special light image. This corresponds to C1 in FIG. 3 and D1 in FIG. 4.

This makes it possible to blend the special light image having a corrected luminance with the normal light image. Since the luminance of the special light image that is normally very dark has been corrected, the normal light image does not become dark even if the blending process is performed, so that the visibility of the lesion area can be improved.

The normal light image acquisition section 320 may acquire the normal light image based on light from a light source having the wavelength band of white light. The special light image acquisition section 330 may acquire the special light image based on light from a light source having the specific wavelength band. In this case, a white light source and a special light source are provided in the light source section 100 instead of the white light source 110.

This makes it possible to acquire the normal light image and the special light image based on the configuration of the light source. Since it is unnecessary to apply a filter or the like, the configuration of the insertion section 200 and the like can be simplified.

The normal light image acquisition section 320 may acquire the normal light image based on light from the light source using a filter that allows light having the wavelength band of white light to pass through. The special light image acquisition section 330 may acquire the special light image based on light from the light source using a filter that allows light having the specific wavelength band to pass through. Specifically, the configuration shown in FIG. 5 may be employed. The imaging element 250 includes the color filter shown in FIG. 6, and the imaging element 260 includes the color filter shown in FIG. 7.

This makes it possible to acquire the normal light image and the special light image based on the configuration of the filter. In this case, a single light source that covers the wavelength band of white light and the wavelength band of special light can be used. Therefore, the configuration of the light source section can be simplified.

This embodiment also relates to an image processing method including acquiring a normal light image that includes an object image and includes information within the wavelength band of white light, acquiring a special light image that includes an object image and includes information within a specific wavelength band, performing a correction process on the special light image, and performing at least one of a first blending process that blends the component G of the normal light image and the component G of the corrected special light image, and a second blending process that blends the component B of the normal light image and the component B of the corrected special light image as a blending process that blends the normal light image and the corrected special light image.

An image in which the visibility of capillaries and a minute mucous membrane pattern in the mucous membrane surface layer is higher than that of the normal light image can be obtained by blending the special light image corrected by the correction section 341 with the normal light image. Moreover, since the components G and the components B are respectively blended, the visibility of the blood vessels and the like can be improved with a natural color.

This embodiment also relates to a program that causes a computer to function as the normal image acquisition section 320, the special light image acquisition section 330, the correction section 341, and the blending section 342. The normal light image acquisition section 320 acquires an image that includes an object image and includes information within the wavelength band of white light, and the special light image acquisition section 330 acquires an image that includes an object image and includes information within a specific wavelength band. The correction section 341 performs the correction process on the special light image, and the blending section 342 performs at least one of a blending process that blends the component G of the normal light image and the component G of the corrected special light image, and a blending process that blends the component B of the normal light image and the component B of the corrected special light image.

This makes it possible to store image data (e.g., capsule endoscope), and process the stored image data by software using a computer system (e.g., PC).

This embodiment also relates to a program that causes a computer to function as the normal image acquisition section 320, the special light image acquisition section 330, and the correction section 341. The normal light image acquisition section 320 acquires an image that includes an object image and includes information within the wavelength band of white light, and the special light image acquisition section 330 acquires an image that includes an object image and includes information within a specific wavelength band. The correction section 341 performs the correction process on the special light image based on the special light luminance information.

This makes it possible to store image data (e.g., capsule endoscope), and process the stored image data by software using a computer system (e.g., PC).

This embodiment also relates to a computer program product that stores a program code that implements each section (normal light image acquisition section, special light image acquisition section, correction section, and blending section) according to this embodiment.

The program code implements the normal light image acquisition section that acquires a normal light image that includes an object image and includes information within the wavelength band of white light, the special light image acquisition section that acquires a special light image that includes an object image and includes information within a specific wavelength band, the correction section that performs a correction process on the special light image, and the blending section that performs a blending process that blends the component G of the normal light image and the component G of the corrected special light image, and a blending process that blends the component B of the normal light image and the component B of the corrected special light image as a blending process that blends the normal light image and the corrected special light image that is the special light image corrected by the correction section.

The term "computer program product" used herein refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to this embodiment are implemented by corresponding modules, and a program code that includes these modules is recorded in the computer program product.

3. Second Embodiment

A method according to this embodiment is described below with reference to FIGS. 19 and 20.

Figure 19:
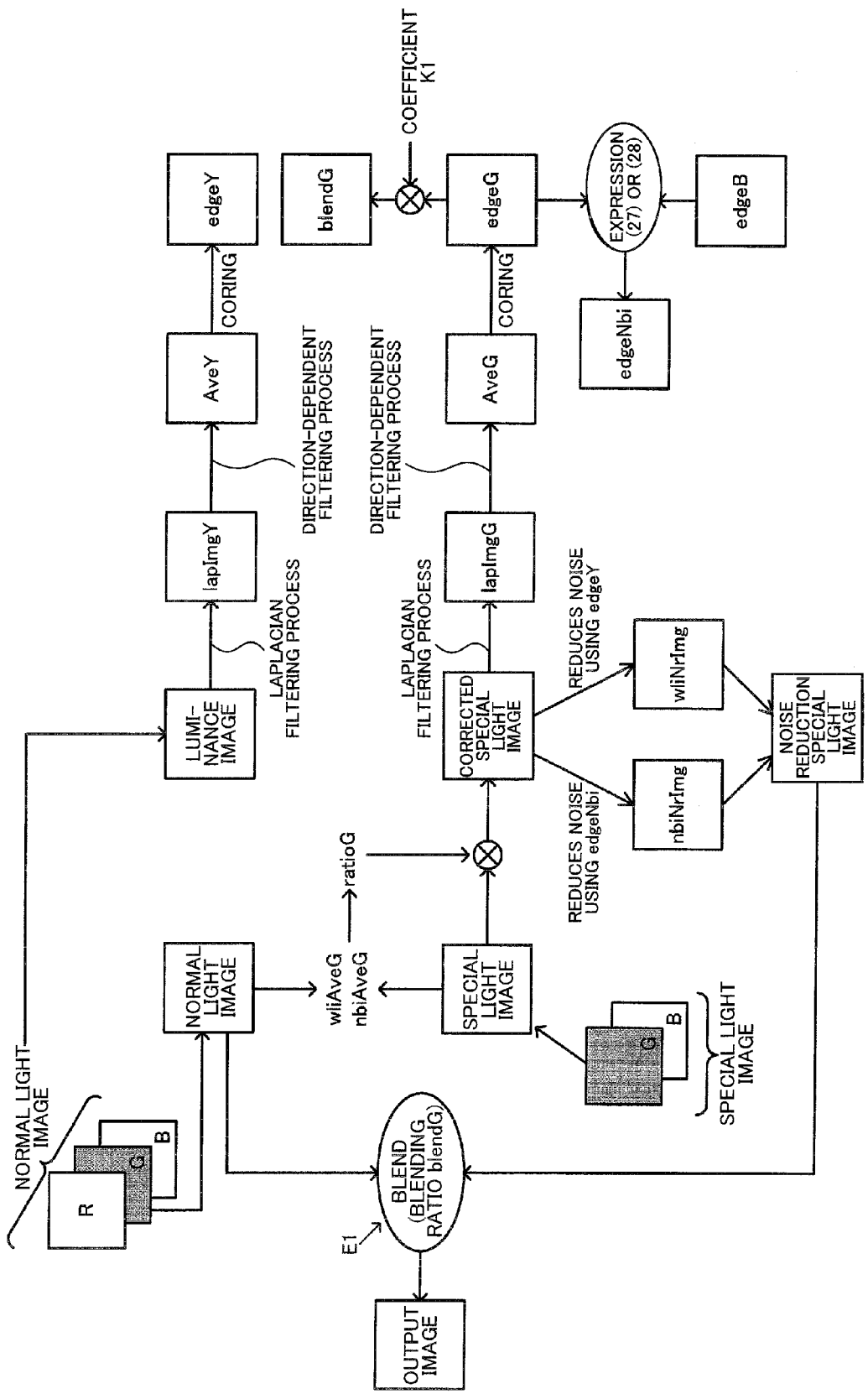
FIG. 19 is another view illustrative of a component G blending process according to one embodiment of the invention.

FIG. 19 is a view illustrative of a component G blending process. The special light image includes components G2 and B2 (when the special light image is an NBI image), and the component G2 is extracted. The normal light image includes components R, G, and B, and the component G that corresponds to the component G2 is extracted.

The ratio ratioG is calculated by the expression (3) from the ratio of the luminance information wliAveG about the component G of the normal light image to the luminance information nbiAveG about the component G2 of the special light image. The luminance of the component G2 of the special light image is corrected by the expression (4) using the ratio ratioG to acquire the corrected special light image (component G).

A noise reduction process is performed on the corrected special light image using an edge information image edgeY of the normal light image to acquire a noise reduction image wliNrImg. The noise reduction process is also performed on the corrected special light image using an edge information image edgeNbi of the normal light image to acquire a noise reduction image nbiNrImg.

The noise reduction image wliNrImg and the noise reduction image nbiNrImg are blended using the expression (30) (described later) to acquire a noise reduction special light image (component G).

The noise reduction special light image (component G) and the normal light image (component G) are blended using the blending ratio blendG to acquire an output image (component G). Note that the process according to this embodiment aims at acquiring the output image. The edge information image edgeNbi, the edge information image edgeY, and the blending ratio blendG are calculated the following process.

When calculating the edge information image edgeNbi, it is necessary to calculate the edge information image edgeG of the component G of the special light image and the edge information image edgeB of the component B of the special light image. The edge information image edgeG and the edge information image edgeB can be calculated by performing the Laplacian filtering process, the direction-dependent filtering process, and the coring process in the same manner as in the first embodiment. The edge information image edgeNbi is calculated by the expression (27) or (28) (described later) using the edge information images edgeG and edgeB thus calculated. The blending ratio blendG can be acquired by multiplying the edge information image edgeG by the coefficient K1.

When calculating the edge information image edgeY, a luminance image is acquired by the expression (26) (described later) using the components R, G, and B of the normal light image. The edge information image edgeY is obtained by subjecting the luminance image to the Laplacian filtering process, the direction-dependent filtering process, and the coring process in the same manner as in the case of the special light image.

Figure 20:
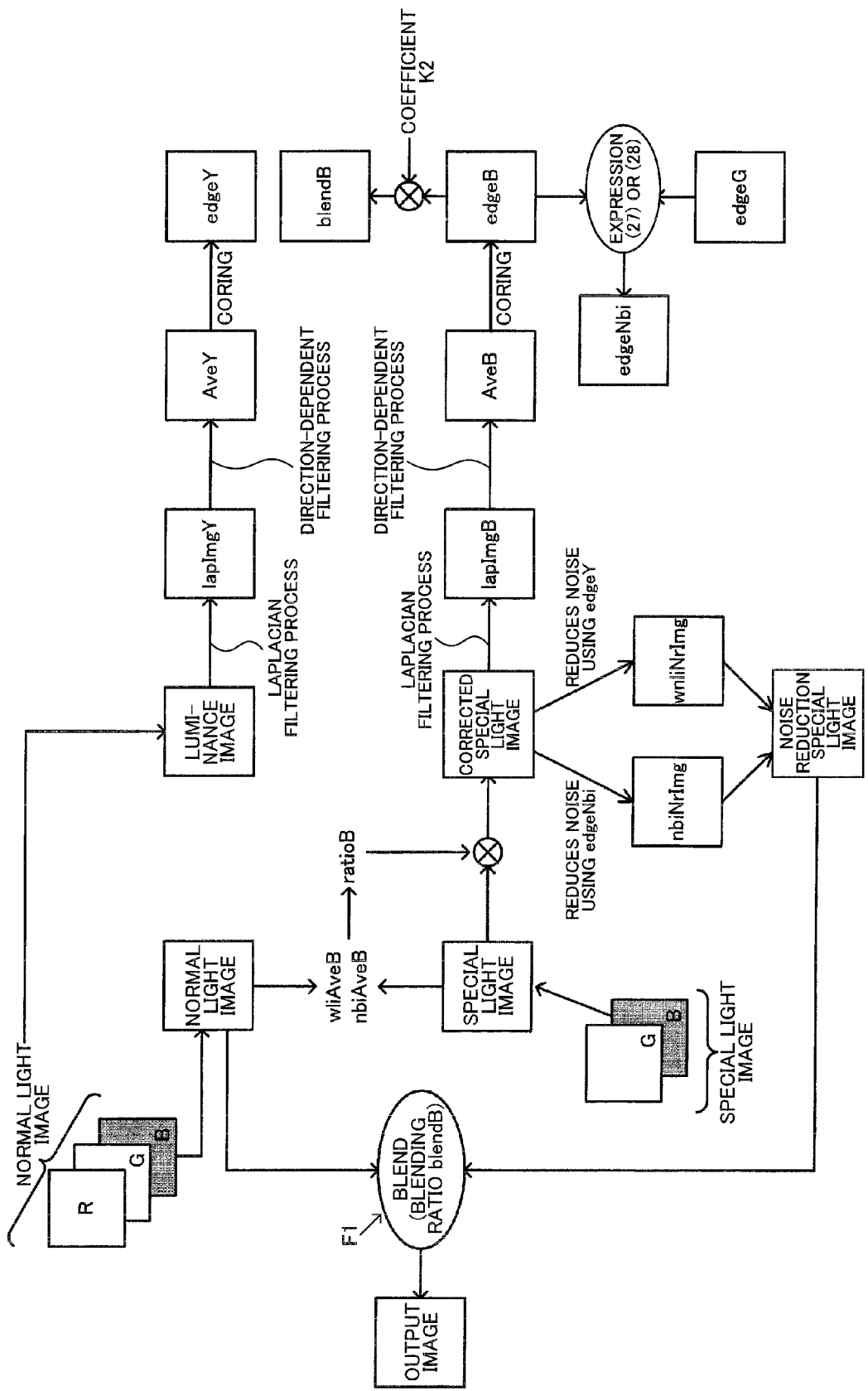
FIG. 20 is another view illustrative of a component B blending process according to one embodiment of the invention.

FIG. 20 schematically shows a component B blending process. Specifically, the corrected special light image (B component) is acquired from the component B2 of the special light image, and subjected to the noise reduction process using the edge information image edgeNbi and the edge information image edgeY to acquire a noise reduction special light image (B component). The noise reduction special light image (component B) and the normal light image (component B) are blended using the blending ratio blendB to acquire an output image (component B).

The component R of the normal light image is directly used in the same manner as in the first embodiment.

A color image is generated based on the components R, B, and G of the output image thus obtained. Since the blood vessels and the like are enhanced in a natural color in the generated image, and noise has been reduced, the burden on the doctor during diagnosis can be reduced, for example.

The system configuration and the above process are described in detail below. Note that detailed description of the configuration and the process similar to those of the first embodiment is omitted.

The configuration according to this embodiment is the same as the configuration according to the first embodiment except for the blending section 342.

Figure 21:
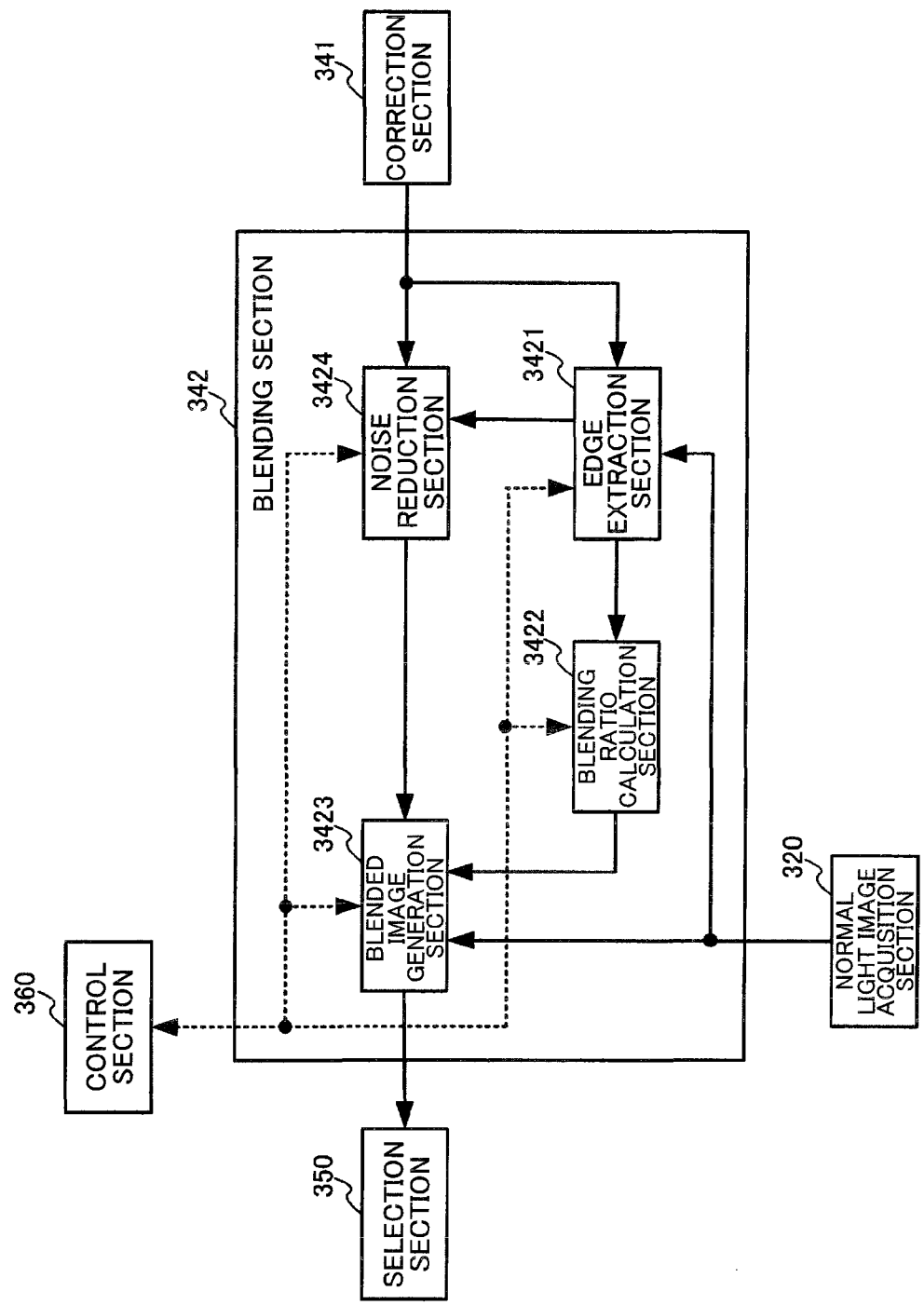
FIG. 21 shows another configuration example of a blending section.

The blending section 342 blends the corrected special light image with the normal light image under control of the control section 360. A specific configuration of the blending section 342 is described later. FIG. 21 is a block diagram illustrative of an example of the configuration of the blending section 342 according to the second embodiment. As shown in FIG. 21, the blending section 342 according to the second embodiment further includes a noise reduction section 3424.

The correction section 341 is connected to the edge extraction section 3421 and the noise reduction section 3424. The edge extraction section 3421 is connected to the blending ratio calculation section 3422 and the noise reduction section 3424. The noise reduction section 3424 is connected to the blended image generation section 3423. The control section 360 is bidirectionally connected to the edge extraction section 3421, the blending ratio calculation section 3422, the blended image generation section 3423, and the noise reduction section 3424, and controls the edge extraction section 3421, the blending ratio calculation section 3422, the blended image generation section 3423, and the noise reduction section 3424.

The edge extraction section 3421 extracts the edge information about the corrected special light image and the edge information about the normal light image. The edge extraction section 3421 performs the direction determination edge extraction process on the luminance signal value Y of the normal light image, the G signal value of the special light image, and the B signal value of the special light image. Specifically, the edge extraction section 3421 calculates the luminance signal value Y of the normal light image by the following expression (26) using the R, G, and B signal values.

$$Y(x,y)=0.213 \times r(x,y)+0.715 \times g(x,y)+0.072 \times b(x,y) \quad (26)$$

The edge extraction section 3421 then performs the process performed on the signals G and B of the special light image (refer to the first embodiment) on the luminance signal value Y of the normal light image. The edge image edgeY of the luminance signal value Y of the normal light image is output to the noise reduction section 3424. The edge image edgeG of the G signal value of the special light image and the edge image edgeB of the B signal value of the special light image generated by a similar process are output to the blending ratio calculation section 3422 and the noise reduction section 3424.

The noise reduction section 3424 performs a noise reduction process on the corrected special light image under control of the control section 360 based on the edge information edgeY about the normal light image or the edge images edgeG and edgeB of the corrected special light image. Specifically, the noise reduction section 3424 blends the edge image edgeG of the G signal value of the special light image and the edge image edgeB of the B signal value of the special light image using the following expression to generate the edge image edgeNbi of the special light image.

$$edgeNbi(x,y)=\text{MAX}(edgeG(x,y),edgeB(x,y)) \quad (27)$$

MAX(a, b) is a function that outputs the larger of a and b. Note that the edge images may be blended as follows.

$$\mathrm{edge}Nbi(x,y) = K3 \times \mathrm{edge}G(x,y) + (1-K3) \times \mathrm{edge}B(x,y) \qquad (28)$$

Note that K3 is a constant term in the range of 0 to 1. A value input in advance from the outside is used as K3.

The noise reduction section 3424 then performs a first noise reduction process on the corrected special light image. Specifically, the noise reduction section 3424 performs a weighted summation process while adding a large weight to a proximate pixel having a value close to that of the attention pixel, and adding a small weight to a proximate pixel having a value that is not close to that of the attention pixel. The noise reduction section 3424 generates a first noise reduction image nbiNrImg by performing a filtering process that implements a weighted summation process while adding a large weight to a proximate pixel having a value close to that of the attention pixel in the edge image edgeNbi of the special light image, and adding a small weight to a proximate pixel having a value that is not close to that of the attention pixel in the edge image edgeNbi of the special light image.

The noise reduction section 3424 then performs a second noise reduction process on the corrected special light image that has not been subjected to the noise reduction process. Specifically, the noise reduction section 3424 generates a second noise reduction image wliNrImg by performing a Gaussian filtering process that decreases the value sigma of the filter when the signal value within the edge image edgeY of the normal light image corresponding to the attention pixel is large, and increases the value sigma of the filter when the signal value within the edge image edgeY is small.

The first noise reduction process is complex as compared with the second noise reduction process since the first noise reduction process is a process based on the edge information about the special light image. Since the special light image is very dark and contains a large amount of noise, noise is carefully reduced by utilizing a complex process so that the process is not affected by noise. Since the first noise reduction process is based on the normal light image that is bright and contains a small amount of noise, only the Gaussian filtering process is used.

The first noise reduction image nbiNrImg and the second noise reduction image wliNrImg are then blended.

$$K5(x,y) = K4 \times \mathrm{edge}Nbi(x,y) \qquad (29)$$

$$nrImg(x,y) = K5(x,y) \times nbiNrImg(x,y) + (1-K5(x,y)) \times wliNrImg(x,y) \qquad (30)$$

Note that K4 is a constant term. K5 is a value in the range of 0 to 1. The image nrImg obtained by the noise reduction process is output to the blended image generation section 3423.

The reasons why the first noise reduction image nbiNrImg and the second noise reduction image wliNrImg are used to calculate the image nrImg, and the edge information image edgeNbi is used when calculating the blending ratio K5 are describe below. In the special light image, a structure (e.g., blood vessel) is enhanced as compared with the normal light image. Therefore, it is preferable that the edge information about the special light image be preferentially reflected in the output image as compared with the edge information about the normal light image. Therefore, the edge information image edgeNbi is used when calculating the blending ratio K5. However, the special light image is very dark, and contains a large amount of noise. When using only the edge information about the special light image, the process may be adversely affected by noise. The effects of noise are reduced by utilizing the edge information about the normal light image that is bright and contains a small amount of noise.

In this embodiment, each section of the image processing section 300 is implemented by hardware. Note that a CPU may perform the process of each section on an image acquired in advance in the same manner as in the first embodiment. Specifically, the process of each section may be implemented by software by causing the CPU to execute a program. Alternatively, part of the process of each section may be implemented by means of software.

Figure 22:
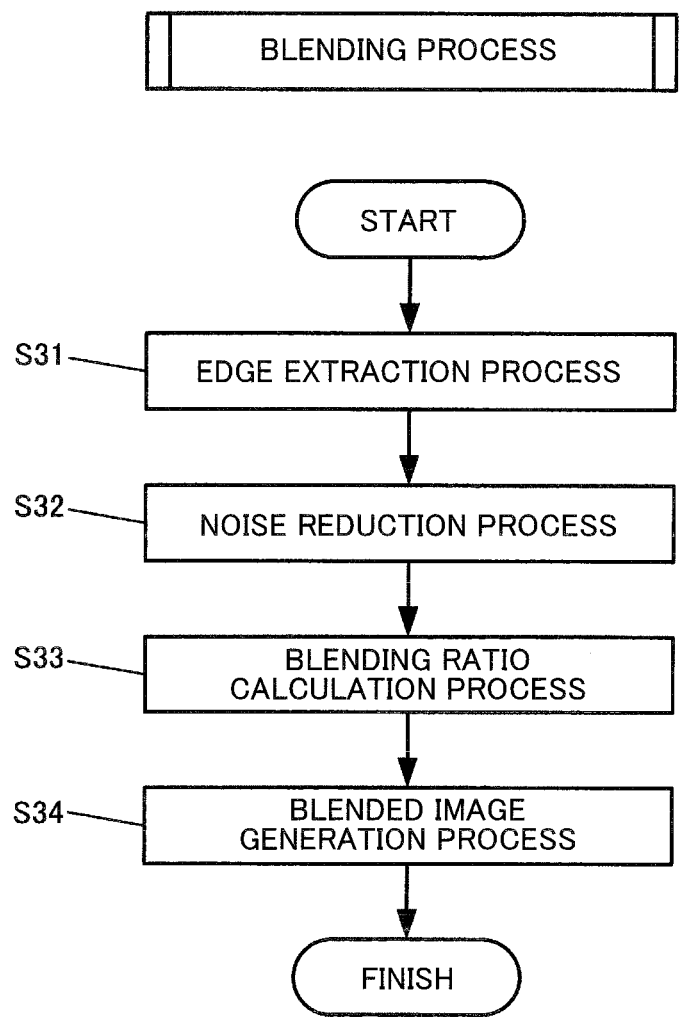
FIG. 22 is a flowchart illustrative of a blending process.

In this case, the process is the same as that of the first embodiment except for the blending process (S16) shown in FIG. 17. The details of the blending process are described below with reference to FIG. 22.

Specifically, the edge information about the corrected special light image and the edge information about the normal light image are extracted using the expressions (8) to (20) (S31). The noise reduction process is then performed on the corrected special light image using the expressions (29) and (30) (S32). The blending ratio is calculated based on the extracted edge information using the expressions (21) and (22) (S33). A blended image is then generated by blending the signals B and G of the normal light image with the signals B and G of the special light image subjected to the noise reduction process using the expressions (23) to (25) (S34).

The above process makes it possible to display the normal light image and the special light image as a single image. Therefore, it is possible to provide an endoscope system that prevents a situation in which a lesion area is missed while reducing the burden on the doctor.

According to this embodiment, the noise reduction section 3424 shown in FIG. 21 performs the noise reduction process on the corrected special light image based on the edge information about the normal light image or the edge information about the corrected special light image. The blending section 342 blends the special light image subjected to the noise reduction process with the normal light image. This corresponds to E1 in FIG. 19 and F1 in FIG. 20.

This makes it possible to reduce the noise level of the special light image that has been increased by the correction process. Therefore, a special light image having a low noise level can be blended with the normal light image. The visibility of the lesion area can be improved by generating a blended image having a low noise level as compared with the case where the noise reduction process is not performed, so that the burden on the doctor can be reduced while preventing a situation in which the lesion area is missed.

The noise reduction section 3424 controls the degree of the noise reduction process based on the edge information about the normal light image. The edge information about the normal light image corresponds to the edge information image edgeY shown in FIGS. 19 and 20. The noise reduction image wliNrImg is acquired by performing the noise reduction process on the corrected special light image using the edge information image edgeY.

The degree of the noise reduction process refers to the value sigma of the Gaussian filtering process, for example.

Therefore, noise can be reduced without impairing the blood vessel information included in the normal light image. The visibility of the lesion area can be improved by generating a blended image having a low noise level, so that the burden on the doctor can be reduced while preventing a situation in which the lesion area is missed.

The noise reduction section 3424 may perform an edge direction determination noise reduction process based on the edge information about the corrected special light image. The edge information about the corrected special light image corresponds to the edge information image edgeNbi shown in FIGS. 19 and 20. The noise reduction image nbiNrImg is acquired by performing the noise reduction process on the corrected special light image using the edge information image edgeNbi.

Therefore, noise can be reduced without impairing the image of capillaries and a minute mucous membrane pattern in the mucous membrane surface layer even if the special light image is very dark. The visibility of the lesion area can be improved by generating a blended image having a low noise level, so that the burden on the doctor can be reduced while preventing a situation in which the lesion area is missed.

The noise reduction section 3424 may perform a weighted summation process as the edge direction determination noise reduction process while adding a large weight to a pixel having a value close to that of the processing target pixel, and adding a small weight to a pixel having a value that is not close to that of the processing target pixel. This corresponds to the nbiNrImg calculation process shown in FIGS. 19 and 20.

This makes it possible to perform the noise reduction process based on the edge direction without impairing the image of capillaries and a minute mucous membrane pattern in the mucous membrane surface layer even if the special light image is very dark.

The first and second embodiments according to the invention and the modifications thereof have been described above. Note that the invention is not limited to the first and second embodiments and the modifications thereof. Various modifications and variations may be made without departing from the scope of the invention. A plurality of elements of each of the first and second embodiments and the modifications thereof may be appropriately combined. For example, some elements may be omitted from the elements of the first and second embodiments and the modifications thereof. The elements described in connection with the above embodiments and the modifications thereof may be appropriately combined. Specifically, various modifications and applications are possible without materially departing from the novel teachings and advantages of the invention.

Any term (e.g., narrow-band light) cited with a different term having a broader meaning or the same meaning (e.g., special light) at least once in the specification and the drawings can be replaced by the different term in any place in the specification and the drawings.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. An image processing device comprising:
a processor; and
a memory storing computer readable instructions that, when executed by the processor, implement:
a normal light image acquisition section that acquires a normal light image that includes an object image and includes information within a wavelength band of white light;
a special light image acquisition section that acquires a special light image that is generated from reflected narrow-band light that differs from the white light, the special light image including a component B corresponding to a surface area of the object and a component G corresponding to a deep area of the object;
a correction section that performs a correction process on the special light image; and
a blending section that performs a blending process that blends the normal light image and a corrected special light image that is the special light image corrected by the correction section,
the blending section performing at least one of a first blending process that blends a component G of the normal light image and the component G of the corrected special light image, and a second blending process that blends a component B of the normal light image and the component B of the corrected special light image as the blending process;
the blending section including:
an edge extraction section that extracts at least one edge information selected from edge information about the corrected special light image and edge information about the normal light image; and
a blending ratio calculation section that calculates a blending ratio based on the at least one edge information extracted by the edge extraction section,
the blending section performing the blending process on the normal light image and the corrected special light image based on the blending ratio calculated by the blending ratio calculation section,
the blending ratio calculation section increasing the blending ratio of the corrected special light image when the amount of edges included in the corrected special light image is large as compared with the blending ratio of the corrected special light image when the amount of edges included in the corrected special light image is small.

2. The image processing device as defined in claim 1,
the edge extraction section extracting the edge information about the corrected special light image by performing an edge detection filtering process including at least a direction-dependent filtering process on the corrected special light image.

3. The image processing device as defined in claim 2,
the edge extraction section extracting the edge information about the corrected special light image by performing a Laplacian filtering process on the corrected special light image, and then performing the direction-dependent filtering process on the corrected special light image.

4. The image processing device as defined in claim 3,
the edge extraction section performing a filtering process that smoothes pixel values of pixels positioned along an edge direction as the direction-dependent filtering process.

5. The image processing device as defined in claim 2,
the edge extraction section extracting the edge information about the normal light image by performing a Laplacian filtering process on the normal light image, and then performing the direction-dependent filtering process on the normal light image.

6. The image processing device as defined in claim 1,
the blending section including:
an attention area detection section that detects an attention area within the corrected special light image;
wherein the blending ratio calculation section calculates the blending ratio based on information about the attention area detected by the attention area detection section.

7. The image processing device as defined in claim 6,
the blending ratio calculation section increasing the blending ratio of the corrected special light image when the attention area has been detected within the corrected special light image as compared with the case where the attention area has not been detected within the corrected special light image.

8. The image processing device as defined in claim 1,
the blending section including a division section that divides the corrected special light image into a plurality of areas; and
the blending ratio calculation section calculating the blending ratio in each of the plurality of areas.

9. The image processing device as defined in claim 1,
the blending section including:
an edge extraction section that extracts at least one edge information selected from edge information about the corrected special light image and edge information about the normal light image; and
a noise reduction section that performs a noise reduction process on the corrected special light image based on the at least one edge information extracted by the edge extraction section,
the blending section performing the blending process on the corrected special light image subjected to the noise reduction process and the normal light image.

10. The image processing device as defined in claim 9,
the noise reduction section controlling the degree of the noise reduction process based on the edge information about the normal light image.

11. The image processing device as defined in claim 9,
the noise reduction section performing an edge direction determination noise reduction process based on the edge information about the corrected special light image.

12. The image processing device as defined in claim 11,
the noise reduction section performing a weighted summation process as the noise reduction process while adding a large weight to a pixel having a value close to that of a processing target pixel, and adding a small weight to a pixel having a value that is not close to that of the processing target pixel.

13. The image processing device as defined in claim 1,
a specific wavelength band of the narrow-band light being narrower than the wavelength band of the white light.

14. The image processing device as defined in claim 13,
the normal light image and the special light image being in vivo images; and
the specific wavelength band included in the in vivo image being a wavelength band of a wavelength absorbed by hemoglobin in blood.

15. The image processing device as defined in claim 14,
the specific wavelength band being 390 to 445 nm or 530 to 550 nm.

16. The image processing device as defined in claim 1,
the normal light image acquisition section acquiring the normal light image based on light from a light source having the wavelength band of the white light; and
the special light image acquisition section acquiring the special light image based on light from a light source having the narrow-band wavelength band.

17. The image processing device as defined in claim 1,
the normal light image acquisition section acquiring the normal light image based on light from a light source using a filter that allows light having the wavelength band of the white light to pass through; and
the special light image acquisition section acquiring the special light image based on light from a light source using a filter that allows light having the narrow-band wavelength band to pass through.

18. An image processing method comprising:
acquiring a normal light image that includes an object image and includes information within a wavelength band of white light;
acquiring a special light image that is generated from reflected narrow-band light that differs from the white light, the special light image including a component B corresponding to a surface area of the object and a component G corresponding to a deep area of the object;
performing a correction process on the special light image; and
performing at least one of a first blending process that blends a component G of the normal light image and the component G of the corrected special light image, and a second blending process that blends a component B of the normal light image and the component B of the corrected special light image as a blending process that blends the normal light image and the corrected special light image;
at least one of the first blending process and the second blending process including the steps of:
extracting at least one edge information selected from edge information about the corrected special light image and edge information about the normal light image;
calculating a blending ratio based on the at least one edge information extracted by the edge extraction; and
performing the blending process on the normal light image and the corrected special light image based on the blending ratio calculated by the blending ratio calculation,
the blending ratio calculation increasing the blending ratio of the corrected special light image when the amount of edges included in the corrected special light image is large as compared with the blending ratio of the corrected special light image when the amount of edges included in the corrected special light image is small.

19. A non-transitory information storage device having stored thereon a program, the program causing a computer to function as:
a normal light image acquisition section that acquires a normal light image that includes an object image and includes information within a wavelength band of white light;
a special light image acquisition section that acquires a special light image that is generated from reflected narrow-band light that differs from the white light, the special light image including a component B corresponding to a surface area of the object and a component G corresponding to a deep area of the object;
a correction section that performs a correction process on the special light image; and
a blending section that performs a blending process that blends the normal light image and a corrected special light image that is the special light image corrected by the correction section, the blending section performing at least one of a first blending process that blends a component G of the normal light image and the component G of the corrected special light image, and a second blending process that blends a component B of the normal light image and the component B of the corrected special light image as the blending process;
the blending section including:
an edge extraction section that extracts at least one edge information selected from edge information about the corrected special light image and edge information about the normal light image; and
a blending ratio calculation section that calculates a blending ratio based on the at least one edge information extracted by the edge extraction section, the blending section performing the blending process on the normal light image and the corrected special light image based on the blending ratio calculated by the blending ratio calculation section, the blending ratio calculation section increasing the blending ratio of the corrected special light image when the amount of edges included in the corrected special light image is large as compared with the blending ratio of the corrected special light image when the amount of edges included in the corrected special light image is small.

* * * * *